US012734072B2

(12) United States Patent
Olson

(10) Patent No.: US 12,734,072 B2
(45) Date of Patent: Sep. 15, 2026

(54) EAR CLEANER DEVICE

(71) Applicant: Quest Products, LLC, Pleasant Prairie, WI (US)

(72) Inventor: Richard Carl Olson, Deerfield Beach, FL (US)

(73) Assignee: Quest Products, LLC, Pleasant Prairie, WI (US)

( * ) Notice: Subject to any disclaimer, the term of this patent is extended or adjusted under 35 U.S.C. 154(b) by 80 days.

(21) Appl. No.: 18/982,870

(22) Filed: Dec. 16, 2024

(65) Prior Publication Data

US 2025/0134719 A1 May 1, 2025

Related U.S. Application Data

(63) Continuation of application No. 17/357,646, filed on Jun. 24, 2021, now Pat. No. 12,186,155, which is a continuation of application No. 16/265,072, filed on Feb. 1, 2019, now Pat. No. 11,045,357, which is a continuation of application No. 15/054,720, filed on Feb. 26, 2016, now Pat. No. 10,219,951, which is a (Continued)

(51) Int. Cl.
*A61F 11/00* (2022.01)
*A61B 17/24* (2006.01)

(52) U.S. Cl.
CPC ............ *A61F 11/006* (2013.01); *A61B 17/24* (2013.01); *A61F 11/00* (2013.01)

(58) Field of Classification Search
CPC ........ A61F 13/38; A61F 11/006; A61F 11/00; A61B 2017/246; A61B 17/244; A61B 17/24; A46B 2200/1006; A61M 2210/0618
See application file for complete search history.

(56) References Cited

U.S. PATENT DOCUMENTS

| | | |
|---|---|---|
| 147,660 A | 2/1874 | Leiner |
| 651,395 A | 6/1900 | Stapp |

(Continued)

FOREIGN PATENT DOCUMENTS

| | | |
|---|---|---|
| AU | 2013100584 | 8/2013 |
| EP | 0158543 | 10/1985 |

(Continued)

OTHER PUBLICATIONS

U.S. Appl. No. 16/265,072, filed Feb. 1, 2019, Richard Carl Olson.

(Continued)

*Primary Examiner* — Majid Jamialahmadi
(74) *Attorney, Agent, or Firm* — Fitch, Even, Tabin & Flannery LLP

(57) ABSTRACT

An ear cleaning device is provided for removing debris from an ear. In one form, the ear cleaning device includes a shaft, a head connected to the shaft, and a contiguous pocket structure of the head. The contiguous pocket structure includes a plurality of pockets that may be configured to receive debris. In another form, the ear cleaning device has a handle, a bulbous cleaner connected to the handle, and a solid inner core of the bulbous cleaner. The bulbous cleaner has two or more spaced, longitudinal walls disposed outward of the inner core that are configured to remove debris with turning of the ear cleaning device about a longitudinal axis of the device.

14 Claims, 32 Drawing Sheets

Related U.S. Application Data continuation of application No. 13/942,267, filed on Jul. 15, 2013, now Pat. No. 9,278,030.

(56) References Cited

U.S. PATENT DOCUMENTS

D144,599 S 4/1946 Tupper
3,099,263 A 7/1963 Palazzolo
3,203,418 A 8/1965 Johnston
4,091,497 A 5/1978 Bade
4,411,265 A 10/1983 Eichenlaub
4,568,326 A 2/1986 Rangaswamy
D296,005 S 5/1988 Alkire
4,746,238 A 5/1988 Levine
4,935,001 A 6/1990 George
5,107,861 A 4/1992 Narboni
D327,322 S 6/1992 Brewer, Jr.
5,223,259 A 6/1993 Lackney
D339,036 S 9/1993 Mcdaniel
5,334,212 A 8/1994 Karell
5,374,276 A 12/1994 Lay
D362,067 S 9/1995 Chang
5,509,921 A 4/1996 Karell
5,632,756 A 5/1997 Kruglick
5,715,559 A * 2/1998 Mitri ...................... A61F 13/38 15/118
5,715,850 A 2/1998 Markgraaf
5,738,643 A 4/1998 Stredic, III
D405,175 S 2/1999 Stredic, III
5,888,199 A 3/1999 Karell
5,897,568 A 4/1999 Vanraes
D414,866 S 10/1999 Szabo
D415,275 S 10/1999 Huttner
D420,133 S 2/2000 Huttner
6,033,417 A 3/2000 Tseng
D422,360 S 4/2000 Young
6,080,126 A 6/2000 Zygmont
D432,239 S 10/2000 Shimizu
D435,295 S 12/2000 Yoo
D441,141 S 4/2001 Shalita
D444,556 S 7/2001 Estrem
6,270,510 B1 8/2001 Westendorf
D469,871 S 2/2003 Sand
6,695,802 B1 2/2004 Thompson
D489,131 S 4/2004 Gojcaj
D489,133 S 4/2004 Shimizu
D490,523 S 5/2004 Samborski
6,736,826 B2 5/2004 Begun
6,939,360 B2 9/2005 Crespo
D515,213 S 2/2006 Huttner
7,070,603 B2 7/2006 Eicoff
7,074,230 B2 7/2006 Olson
D526,061 S 8/2006 Nam
D545,431 S 6/2007 Khademhosseini
D546,948 S 7/2007 Huttner
D547,869 S 7/2007 Eckman
D560,800 S 1/2008 Curtis
D560,806 S 1/2008 Eckman
D567,373 S 4/2008 Irby
D603,046 S 10/2009 Frey
7,658,745 B2 2/2010 Olson
D631,957 S 2/2011 Perez
D638,985 S 5/2011 Limongi
7,951,106 B1 5/2011 Perez
D654,165 S 2/2012 Yates
D701,600 S 3/2014 Kauffman
9,232,853 B2 1/2016 Olson
9,233,027 B1 1/2016 Jackson
9,278,030 B2 3/2016 Olson
D757,938 S 5/2016 Jackson
10,219,951 B2 3/2019 Olson
D847,993 S 5/2019 Olson
10,479,842 B2 11/2019 Haley
10,531,986 B2 1/2020 Olson
D921,897 S 6/2021 Chi
11,045,357 B2 6/2021 Olson
D952,849 S 5/2022 Olson
D980,980 S 3/2023 Chi
11,890,167 B2 2/2024 Olson
D1,059,883 S 2/2025 Xiong
2001/0001828 A1 5/2001 Begun
2003/0135228 A1 7/2003 Crespo
2003/0187469 A1 10/2003 Olson
2003/0225431 A1 12/2003 Yoo
2005/0027315 A1 2/2005 Plateroti
2005/0070948 A1 3/2005 Kirsteins
2005/0096678 A1 5/2005 Olson
2005/0154429 A1 7/2005 Huang
2005/0267507 A1 12/2005 Kao
2008/0300527 A1 12/2008 Bivins
2009/0248029 A1 10/2009 Paulos
2010/0312198 A1 12/2010 Guidi
2010/0330136 A1 12/2010 Rocabayera Bonvila
2011/0179887 A1 7/2011 Cobian
2012/0296355 A1 11/2012 Burres
2013/0331804 A1 12/2013 Nino
2014/0031846 A1 1/2014 Edme
2014/0276893 A1 9/2014 Schaller
2015/0018861 A1 1/2015 Olson
2016/0175154 A1 6/2016 Olson
2017/0087024 A1 3/2017 Al-Bakkour
2017/0354541 A1 12/2017 Olson
2019/0159936 A1 5/2019 Olson
2020/0214895 A1 7/2020 Olson
2021/0346206 A1 11/2021 Olson
2021/0378912 A1 12/2021 Nakano
2021/0378913 A1 12/2021 Nakano
2021/0403228 A1 12/2021 Nakano
2024/0225901 A1 7/2024 Olson

FOREIGN PATENT DOCUMENTS

EP 0234061 9/1987
EP 0875221 11/1998
WO 1996037172 11/1996

OTHER PUBLICATIONS

U.S. Appl. No. 29/567,975, filed Jun. 14, 2016, Richard Carl Olson.

"Ototek Loop Ear Wax Removal." <https://www.amazon.com/Ototek-Loop-Ear-Wax-Removal/product-reviews/B008BXLINQ/ref=cm_cr_getr d_paging_btm_next_35?ie=UTF8&reviewerType=all_reviews&sortBy=recent&pageNumber=35>, Aug. 13, 2012, 3 pages.

"Pictures of an Ear Cleaning Device and Its Retail Packaging." The ear cleaning device being publicly available before Jun. 14, 2016, 3 pages.

"Pictures of Another Clinere® Brand Ear Cleaner." The ear cleaning device being publicly available for purchase more than one year before Jul. 15, 2013, 3 pages.

"Pictures of Clinere® Brand Ear Cleaner." The ear cleaning device being publicly available for purchase more than one year before Jul. 15, 2013, 3 pages.

"Pictures of Ear Cleaner—Earvana 1." The ear cleaner being publicly available before Mar. 2013, 2 pages.

"Pictures of Ear Cleaner—Earvana 2." The ear cleaner being publicly available before Mar. 2013, 2 pages.

"Pictures of Ear Cleaner—Earvana 3." The ear cleaner being publicly available before Mar. 2013, 2 pages.

"Pictures of Ear Cleaner—Earvana 4." The ear cleaner being publicly available before Mar. 2013, 2 pages.

"Pictures of Ear Scrubber Ear Cleaner." The ear cleaner being publicly available Nov. 2015, 1 page.

"Pictures of Ototek Loop Ear Cleaner." The ear cleaner being publicly available for sale before Jul. 15, 2012, 3 pages.

"Pictures of Walgreens Brand Ear Cleaner." The ear cleaning device being publicly available for purchase on or about Jun. 29, 2017, 3 pages.

Clinere Earwax Cleaning Kit https://www.amazon.com/Clinere-Earwax-Cleaning-Kit/dp/BO101K30Pl/ref=sr_1 _3_s_it?s=hpc&ie=

(56) References Cited

OTHER PUBLICATIONS

UTF8&qid=1522946098&sr=1-3&keywords=clinere#customerReviews Jan. 7, 2017 (Year: 2017).
Final Office Action, U.S. Appl. No. 17/357,646, dated Jun. 2, 2023, 14 pages.
Final Office Action, U.S. Appl. No. 17/357,646, dated Apr. 18, 2024, 18 pages.
Office Action, U.S. Appl. No. 17/357,646, dated Dec. 2, 2022, 15 pages.
Office Action, U.S. Appl. No. 17/357,646, dated Sep. 22, 2023, 15 pages.
Ototek Loop Ear Wax Removal https://www.amazon.com/Ototek-Loop-Ear-Wax-Removal/dp/B008BXLINQ/ref=cm_cr_arp_d_product_top?ie=UTF8 Aug. 13, 2012 (Year: 2012).
Response to Office Action filed May 20, 2005, from U.S. Appl. No. 10/369,915, 4 pages.
Response to Office Action filed Office Action dated Jan. 5, 2006, from U.S. Appl. No. 10/369,915, 8 pages.
U.S. Patent and Trademark Office, Non-Final Office Action issued in U.S. Appl. No. 18/205,253, filed Aug. 7, 2023, 11 pp.
U.S. Appl. No. 15/655,332, "Ear Cleaner," filed Jul. 20, 2017, 10 pages.
U.S. Appl. No. 16/739,859, "Ear Cleaner," filed Jan. 10, 2020.
U.S. Appl. No. 29/836,835, "Ear Cleaner," filed Apr. 29, 2022, 14 pages.
United States Patent Office, Office Action dated Apr. 16, 2018, from related U.S. Appl. No. 29/567,975, 12 pages.
YouTube video entitled "Smart Swab," posted Sep. 4, 2014, screen captures and video description, 5 pages. <https://youtu.be/XNSpdXUwNuM>.

* cited by examiner 21
21
702
706
704
710
700

26
26
806
804
808

902
28
28
906
904
908

900

EAR CLEANER DEVICE

CROSS-REFERENCE TO RELATED APPLICATIONS

This application is a continuation of U.S. patent application Ser. No. 17/357,646, filed Jun. 24, 2021, which is a continuation of U.S. patent application Ser. No. 16/265,072, filed Feb. 1, 2019, now U.S. Pat. No. 11,045,357, which is a continuation of U.S. patent application Ser. No. 15/054,720, filed Feb. 26, 2016, now U.S. Pat. No. 10,219,951, which is a continuation of U.S. patent application Ser. No. 13/942,267, filed Jul. 15, 2013, now U.S. Pat. No. 9,278,030, which are hereby incorporated herein by reference in their entireties.

FIELD

This invention relates to an ear cleaning device for removing debris from an ear.

BACKGROUND

One prior approach for removing debris, such as ear wax, from an ear involves inserting a cotton swab into the ear and manipulating the cotton swab within the ear. Although this approach is commonly used, it has significant problems. For example, moving the cotton swab within the ear tends to smear ear wax against the ear canal rather than removing the ear wax. Further, the cotton swab may push the wax deeper into the ear and/or compact the wax making it more difficult to remove at a later time.

DETAILED DESCRIPTION

Figure 1:
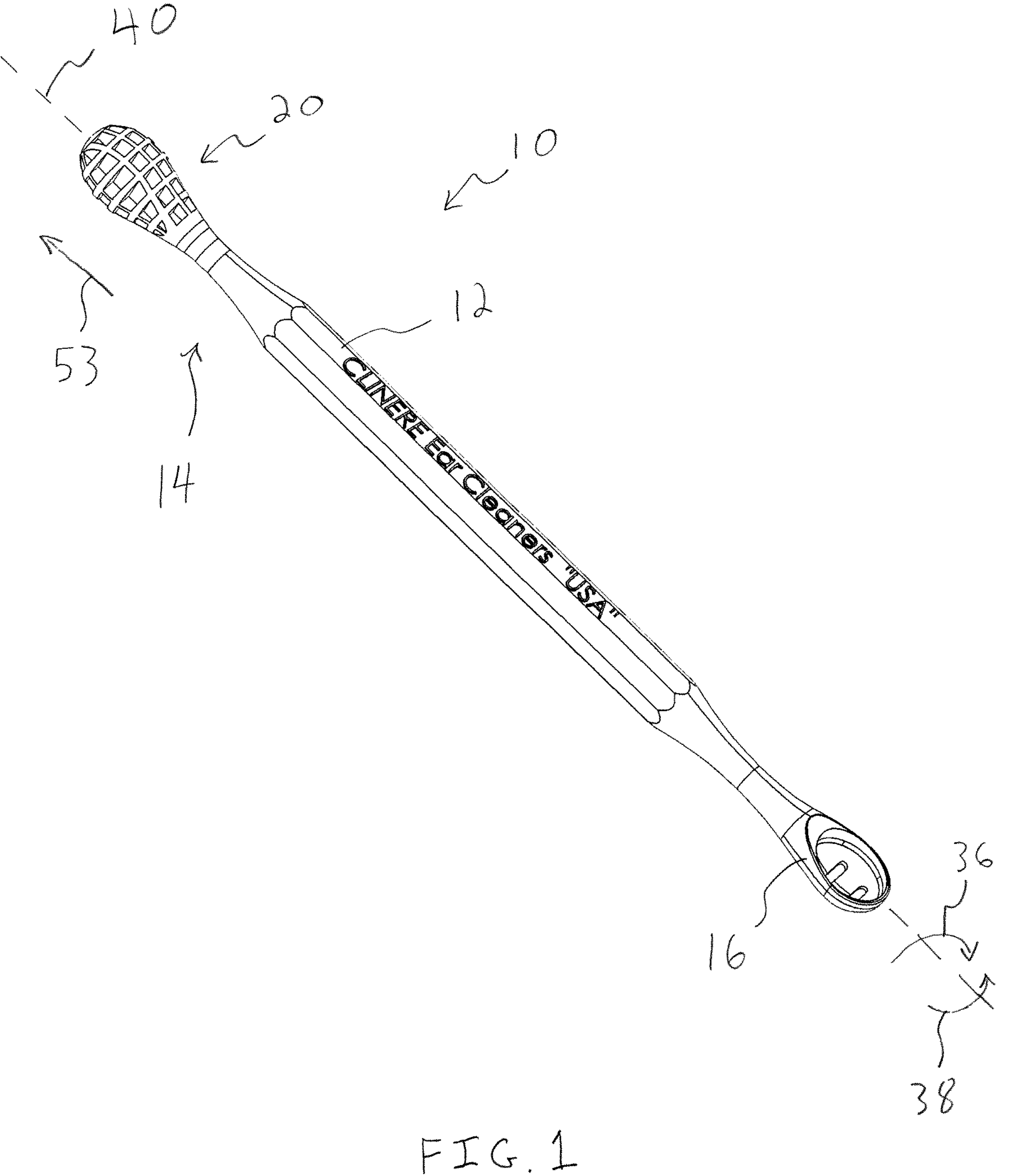
FIG. 1 is a perspective view of an ear cleaning device.

An ear cleaning device is disclosed that provides improved removal of debris from an ear surface using at least one of generally rotary movement of the ear cleaning device against the ear surface and generally linear movement of the ear cleaning device against the ear surface. In one form, the ear cleaning device is an elongate ear cleaning device having a predetermined length, a head, and a contiguous pocket structure of the head including a plurality of pockets. The pockets include edges extending along the length of the ear cleaning device that are configured to lift or scrape debris from an ear surface so that the debris can be captured within the pockets for subsequent removal from the ear. In this manner, a user can advance the head of the ear cleaning device into contact with an ear surface and turn the ear cleaning device about a longitudinal axis thereof. This turning movement causes the longitudinal edges and pockets to be sequentially presented to the ear surface so that the edges lift debris from the ear surface which can then be captured within the pockets. Alternatively or in addition to using rotary movement of the ear cleaning device to remove debris, the user may also utilize linear movement of the ear cleaning device to remove debris from the ear surface. More specifically, the pockets may also have lateral edges extending transverse to the length of the ear cleaning device that are configured to lift or scrape debris from the ear surface. These lateral edges permit a user to advance the head of the ear cleaning device into contact with an ear surface and move the device linearly to lift or scrape debris into the head pockets for removal. The ear cleaning device thereby permits the user to remove and capture ear surface debris with linear movement of the device rather than smearing or compacting as with conventional cotton swabs.

In another form, the ear cleaning device has a bulbous cleaner connected to a handle and a solid inner core of the bulbous cleaner. The bulbous cleaner has two or more spaced, longitudinal walls disposed outward of the solid inner core. The spaced, longitudinal walls extend along a longitudinal axis of the ear cleaning device and are configured to remove debris from an ear with turning of the ear cleaning device about the longitudinal axis thereof. A user may thereby advance the bulbous cleaner into position against an ear surface and turn the device about the longitudinal axis to bring the head longitudinal walls into contact with the ear surface one longitudinal wall after the other to lift or scrape debris away from the ear surface. The ear cleaning device is therefore well-suited for use by persons who instinctively rotate ear cleaning devices to remove ear surface debris. In one form, the bulbous cleaner includes a wall oriented to extend transverse to the spaced, longitudinal walls and configured to remove debris from the ear with longitudinal movement of the device. In this manner, the ear cleaning device provides effective and easy-to-use surface debris removal with either rotary or linear movement of the ear cleaning device.

Figure 2:
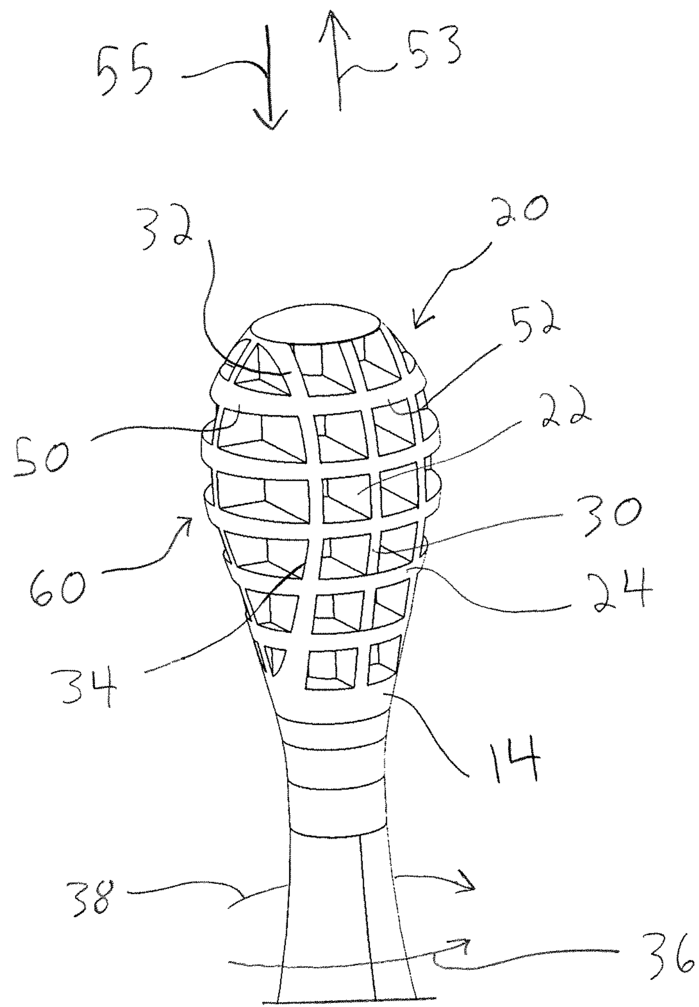
FIG. 2 is an enlarged perspective view of a head of the ear cleaning device of FIG. 1.
Figure 3:
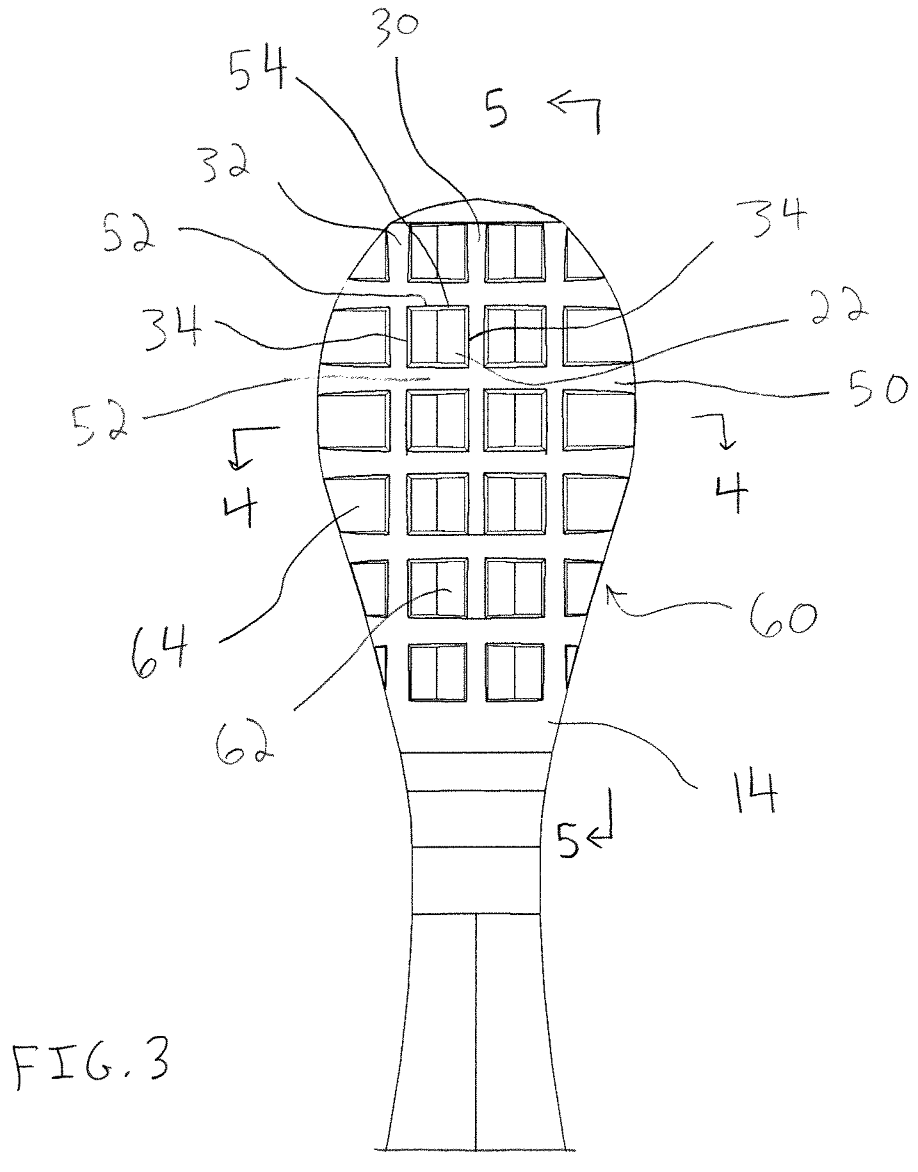
FIG. 3 is a front elevational view of the head of FIG. 2.

With reference to FIGS. 1-5, an ear cleaning device 10 is shown having a generally elongate configuration including a body, such as shaft 12, with a head 14 connected at one end of the shaft 12 and a utensil, such as scoop 16, connected at the other end of the shaft 12. The head 14 has a generally bulbous shape with a contiguous pocket structure 20 thereon that includes a plurality of pockets 22, as shown in FIGS. 2 and 3. The head 14 has an outer surface 24 and the pockets 22 preferably cover more than half of the outer surface 24 of the head 14 and, in some approaches, the pockets 22 cover substantially the entire outer surface 24 of the head 14. The extensive coverage of the pockets 22 about the head 14 provides many different locations to store ear debris such that the head 14 need not be oriented in a precise manner against an ear surface to remove debris therefrom. This improves ease of use of the device 10. Further, the many pockets 22 about the head 14 provides the head 14 with the ability to store and remove a relatively large volume of debris from an ear.

With respect to FIG. 2, the contiguous pocket structure 20 includes longitudinal members such as longitudinal walls 30, 32 having edges 34 thereof configured to lift or scrape debris from an ear with turning of the ear cleaning device 10 in directions 36 or 38 about a longitudinal axis 40 of the ear cleaning device 10, as shown in FIG. 1. The scraping edges 34 direct the debris into the pockets 22 where the debris can be retained until the ear cleaning device 10 is removed from the ear. The contiguous pocket structure 20 may also include transverse members such as lateral walls 50 with edges 52 configured to lift or scrape debris with generally linear movement of the head 14 in directions 53, 55, as shown in FIG. 2. Thus, a user can bring the head 14 into contact with surface(s) of an ear and apply linear and/or rotary movement in directions 36, 38, 53, 55 to engage the edges 34, 52 with the ear surface(s) and lift or scrape debris from the surface(s) which can then be captured within the pockets 22 for later removal. Thus, the device 10 is effective at removing debris using both linear and rotary movement.

With reference to FIG. 3, the edges 34, 52 define openings 54 of the pockets 22. As discussed in greater detail below, the pockets 22 and openings 54 thereof may be arranged in a repeating pattern about the head 14 that can be, for example, an alternating, offset, or aligned pattern, or a combination of different patterns. Further, the pockets 22 and openings thereof may have the same or varying sizes about the head 14. Still further, the pockets 22 and openings 54 thereof can have the same shape, such as hexagonal, or may have different shapes, such as the interior of the pocket 22 having a polygonal shape and the openings 54 having a circular shape. The many different possible combinations of patterns, positioning, sizing, etc. of the pockets 22 and openings 54 thereof allows the debris removal abilities of the head 14 to be narrowly tailored as desired by a device manufacturer. As but one example in this regard, the pockets 22 and openings 54 near a distal end of the head 14 may be smaller for initially breaking up debris using a linear movement of the device 10 in directions 53, 55 against the ear surface (see FIG. 2) whereas the pockets 22 and openings 54 along the sides of the head 14 may be larger for subsequently capturing and removing the debris using rotary movement of the device 10 in directions 36, 38 against the ear surface.

Figure 4:
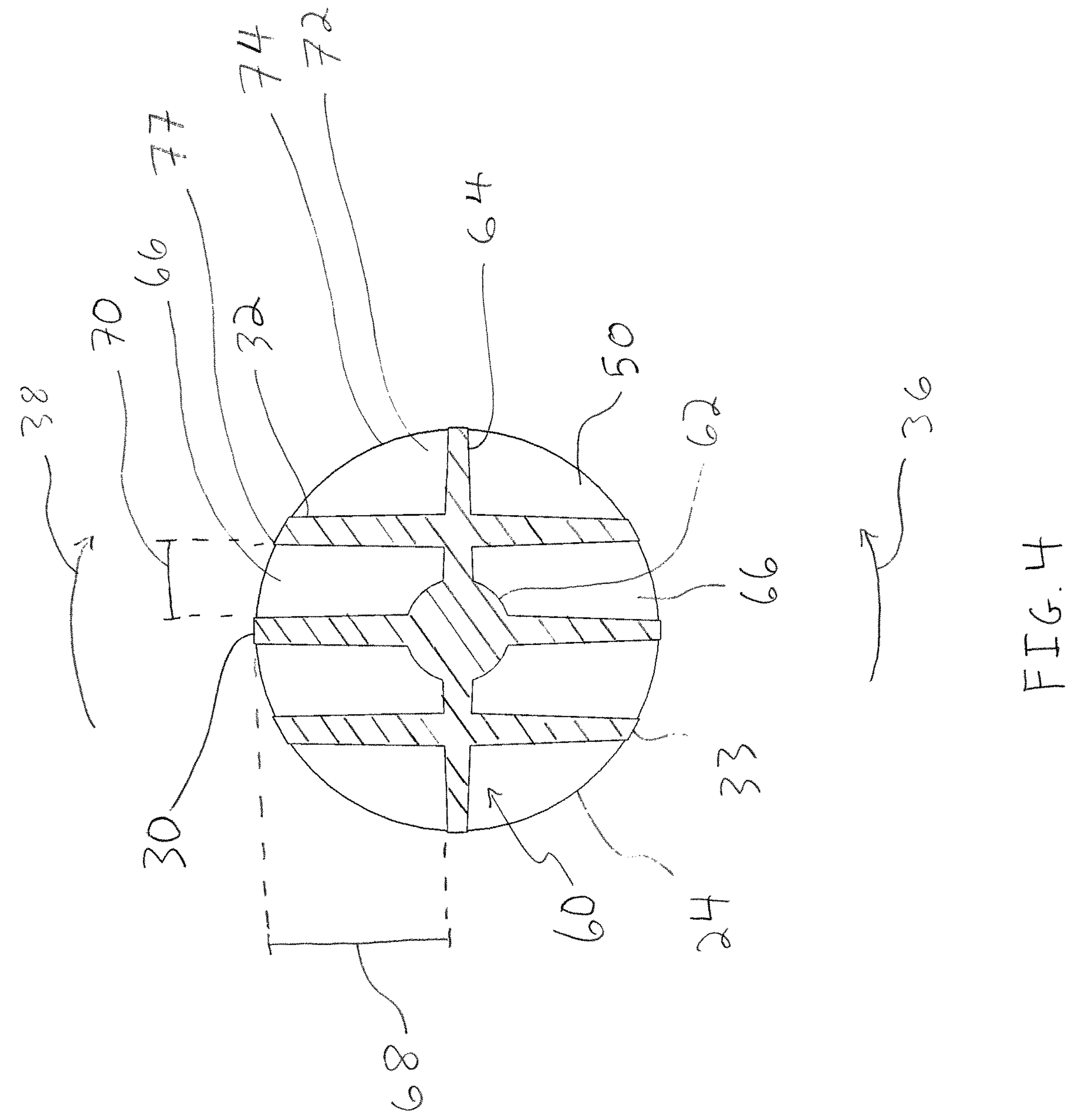
FIG. 4 is a cross-sectional view taken across line 4-4 in FIG. 3.

As shown in FIGS. 3 and 4, the head 14 has a solid inner core 60 to support the contiguous pocket structure 20 and resist bending and twisting of the head 14 during use of the device 10. The solid inner core 60 includes a central support shaft 62 and a support wall 64 extending outwardly from the central support shaft 62. Although the support shaft 62 is shown as having a cylindrical configuration with the support wall 64 extending radially outward therefrom, it will be appreciated that the support shaft 62 and support wall 64 can have many different shapes and orientations. For example, the support wall 64 may have through openings therein such that side pockets 66 (see FIG. 4) on opposite sides of the support wall 64 are in communication with one another.

In the form shown in FIGS. 2 and 3, the contiguous pocket structure 20 has an aligned, generally grid-like pattern of the pockets 22 on the head 14 with the pockets 22 and openings 54 thereof aligned along a length 55 (see FIG. 5) of the head 14 as well as circumferentially about the head 14. With reference to FIG. 4, the longitudinal walls 30, 32 extend outward from the support wall 64 and define generally rectangular side pockets 66 having a depth 68 from the head outer surface 24 to the support wall 64. Further, the longitudinal walls 30, 32 are spaced apart from one another to define a width 70 of the side pockets 66. The pockets 22 may also include corner pockets 72 having a generally pie-shaped configuration defined in part by the longitudinal wall 32 and the support wall 64. The corner pockets 72 have a larger opening 74 along the head outer surface 24 than the side pockets 66 (see FIG. 3), but a smaller overall depth due to the position of the corner pocket 72 around the circumference of the head 14 (see FIG. 4).

Figure 5:
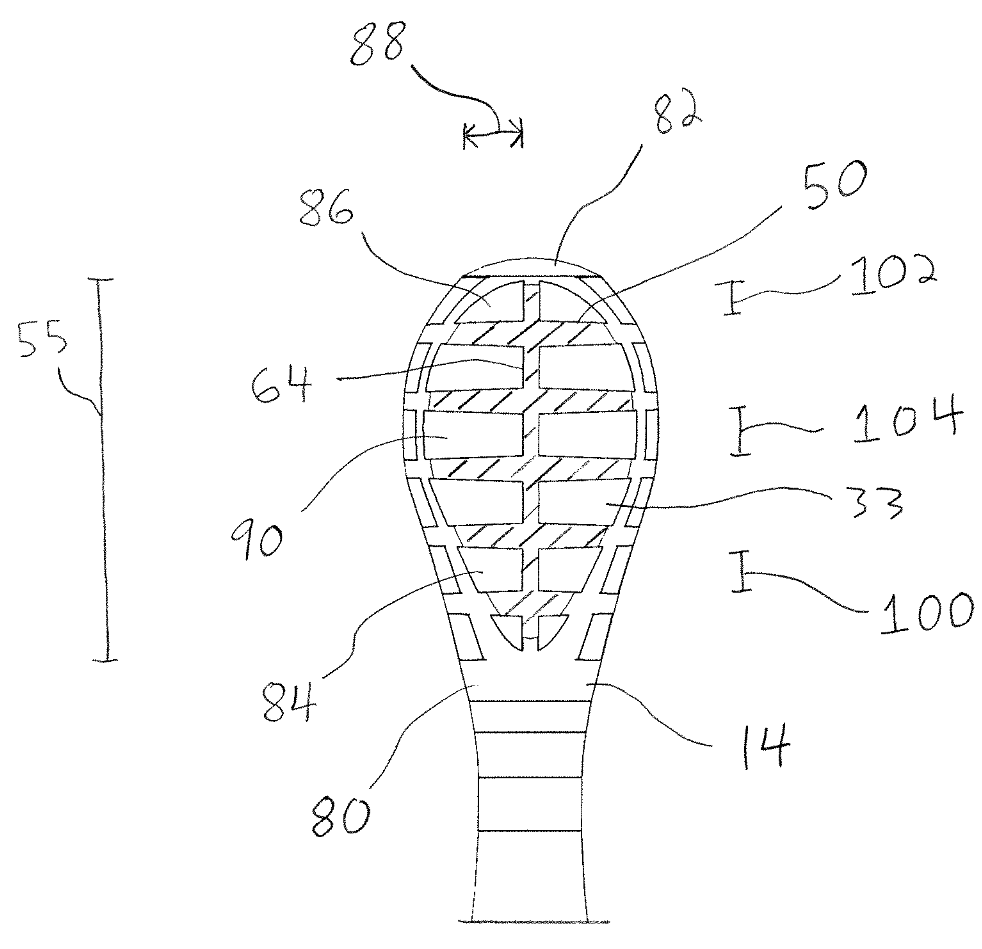
FIG. 5 is a cross-sectional view taken across line 5-5 in FIG. 3.

With reference to FIG. 5, a depth 88 of the pockets 22 varies along the length 55 of the head 14 from a base end 80 of the head 14 to a tip end 82 of the head 14. More specifically, the pockets 22 include pole pockets 84, 86 near the ends 80, 82 having depths 88 that are less than the depths 88 of equator pockets 90. However, the pole pockets 84, 86 and equator pockets 90 have similar heights 100, 102, 104 between the lateral walls 50.

Figure 6:
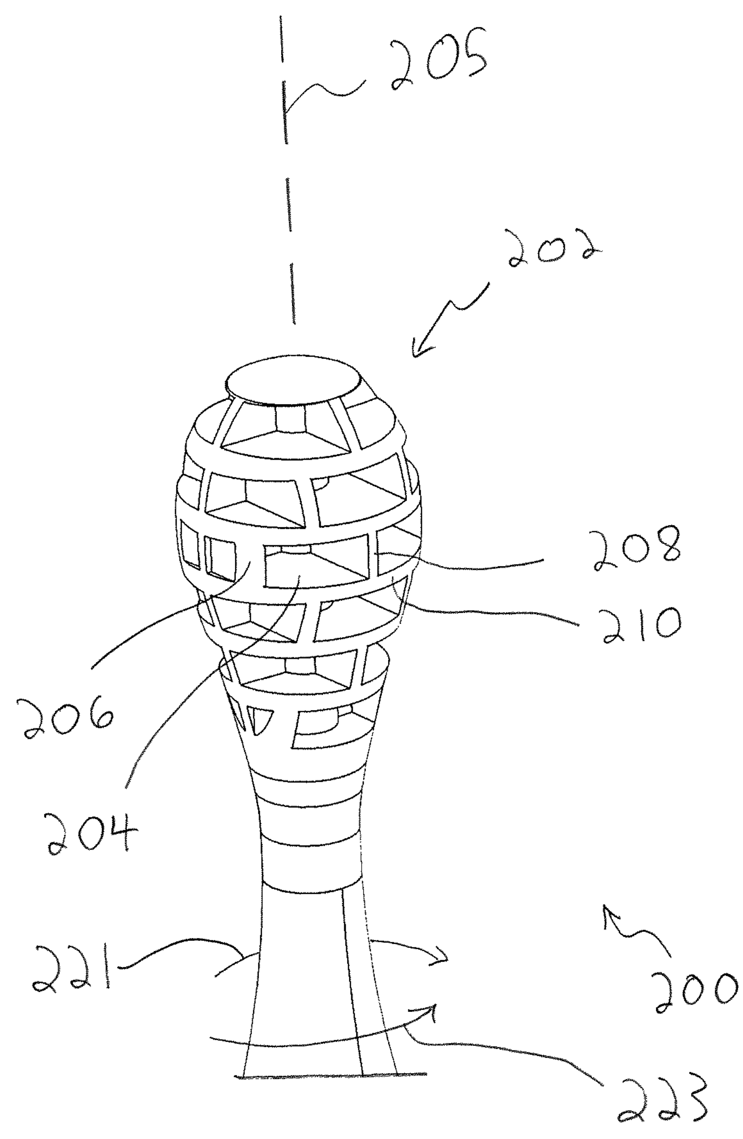
FIG. 6 is a perspective view of another head for the ear cleaning device of FIG. 1.
Figure 7:
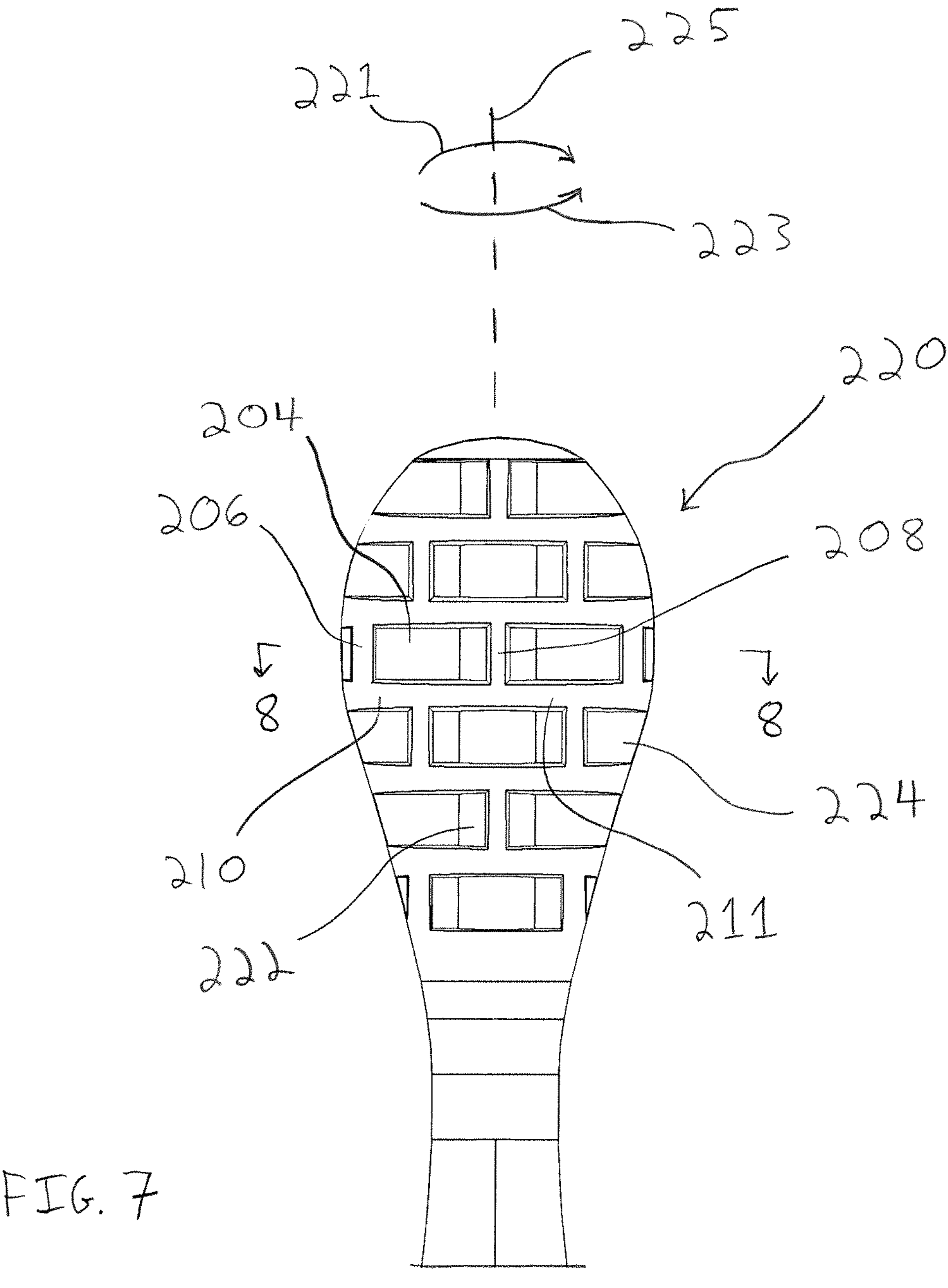
FIG. 7 is a front elevational view of the head of FIG. 6.
Figure 8:
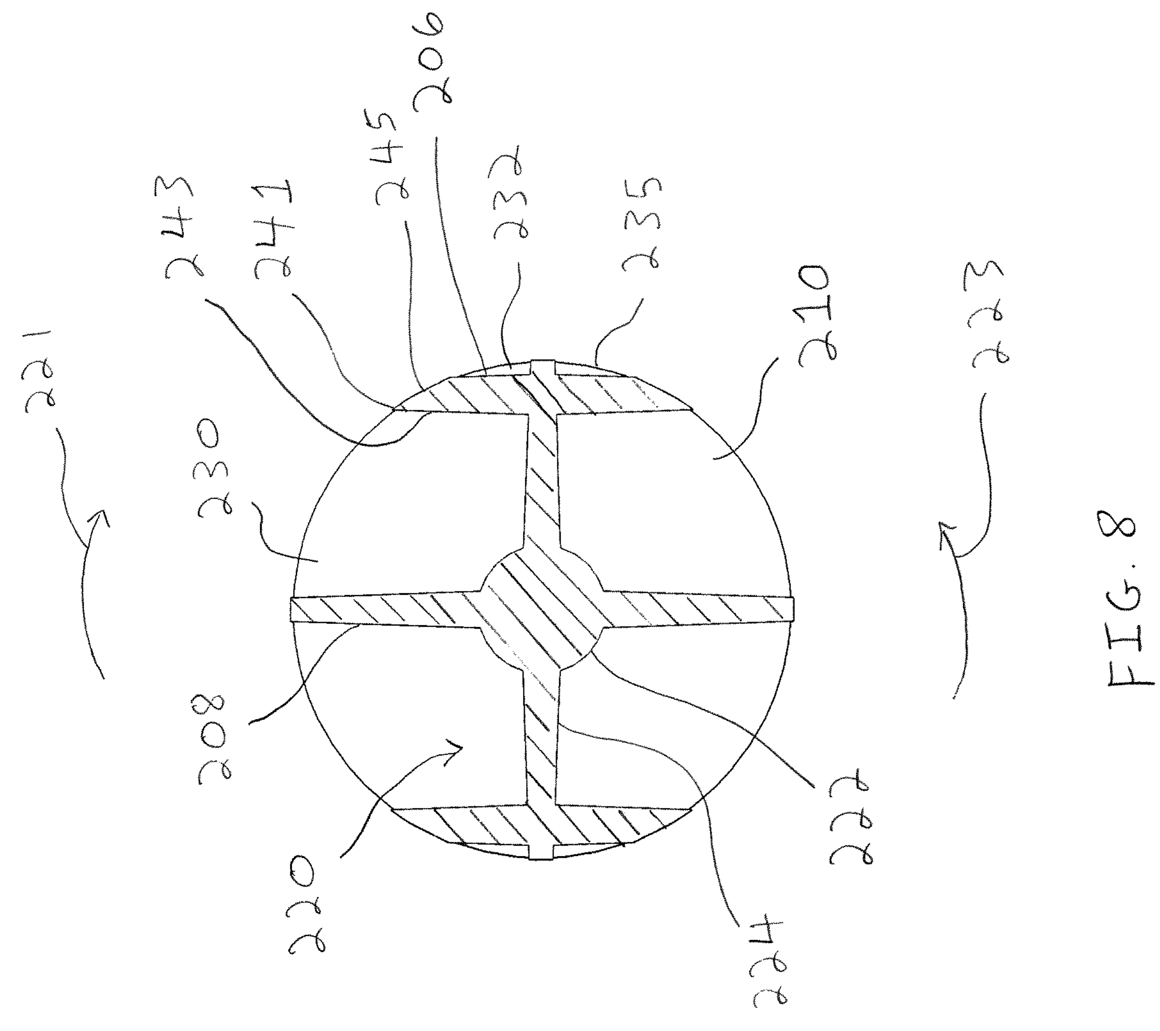
FIG. 8 is a cross-sectional view taken across line 8-8 in FIG. 7.

With reference to FIGS. 6-8, another head 200 for the ear cleaning device 10 is shown. The head 200 is similar to the head 14 such that differences between the two will be highlighted. For example, the head 200 has a contiguous pocket structure 202 with a number of pockets 204 arranged in a grid-like pattern where the pockets 204 are offset along a longitudinal axis 205 of the head 200 while being aligned along the circumference of the head 200. With reference to FIGS. 6 and 7, the pocket structure 202 includes longitudinal walls 206, 208 and lateral walls 210 defining the pockets 204. Although the longitudinal walls 206, 208 are longitudinally offset from one row of pockets 204 to the next, the longitudinal walls 206, 208 still lift or scrape debris from ear surfaces with turning of the head 200 in directions 221, 223 about the longitudinal axis 205 of the head 200, as shown in FIGS. 7 and 8.

With reference to FIGS. 7 and 8, the head 200 includes a solid inner core 220 including an inner support shaft 222 and a support wall 224 to support the contiguous pocket structure 202. The pocket structure 202 has fewer pockets 204 than the pocket structure 20 of head 10 but the pocket structure 202 includes side pockets 230 (see FIG. 8) that are larger than the side pockets 66 of the head 14 (see FIG. 4). The side pockets 230 may therefore be able to capture larger pieces of debris than the side pockets 66. Although the side pockets 230 are larger than the side pockets 66, the pocket structure 202 has corner pockets 232 (see FIG. 9) that are smaller than the corner pockets 50 of the head 20 (see FIG. 4). The corner pockets 232 are smaller because the longitudinal wall 206 of the pockets 232 (see FIG. 8) is positioned closer to an outer surface 235 of the head 200 than the longitudinal wall 32 is positioned near the outer surface 24 of the head 14 (see FIG. 4). This configuration of the outer longitudinal wall 206 forms an outer edge 241 of the outer longitudinal wall 206 (see FIG. 8) that is sharper than an outer edge 77 of the outer longitudinal wall 32 (see FIG. 4). The head 200 may therefore be included in the device 10 when more aggressive scraping of an ear surface is desired.

Figure 9:
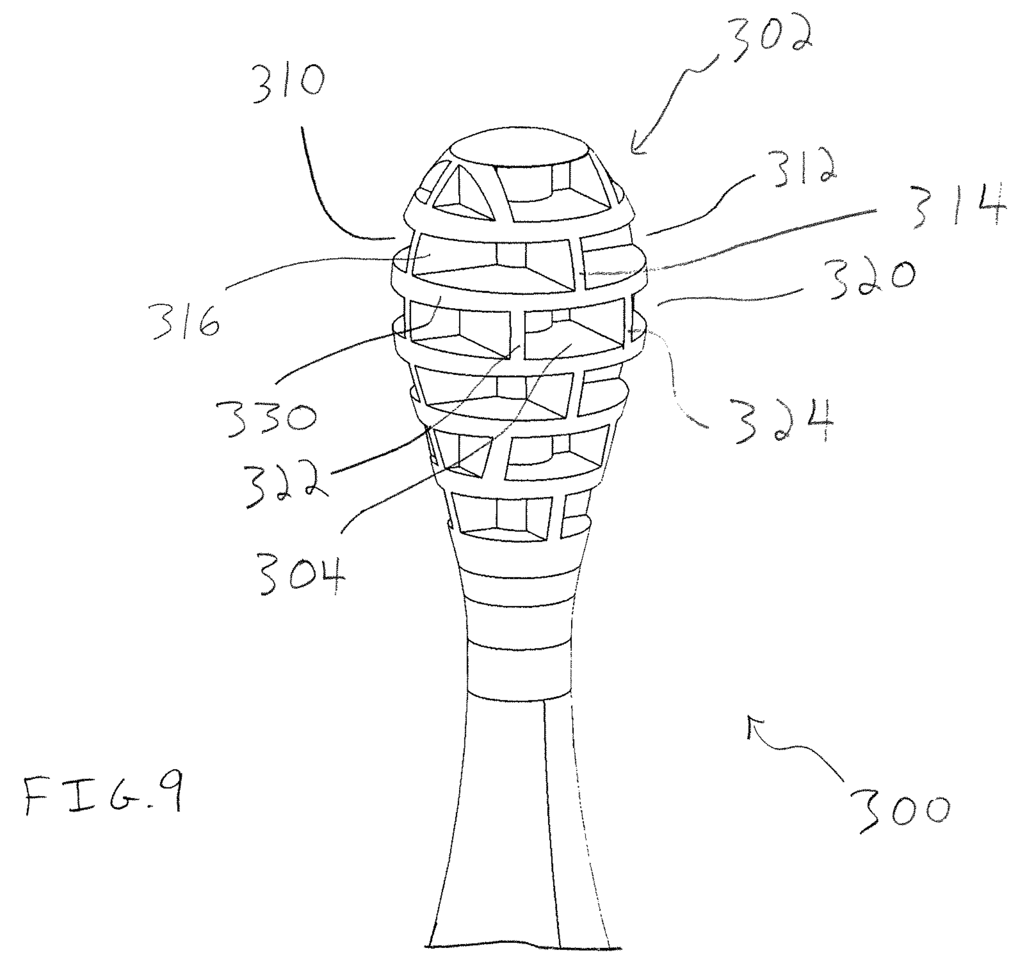
FIG. 9 is a perspective view of another head for the ear cleaning device of FIG. 1.
Figure 10:
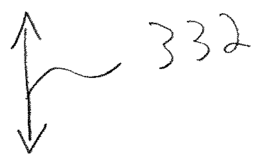
FIG. 10 is a front elevational view of the head of FIG. 9.
Figure 10:
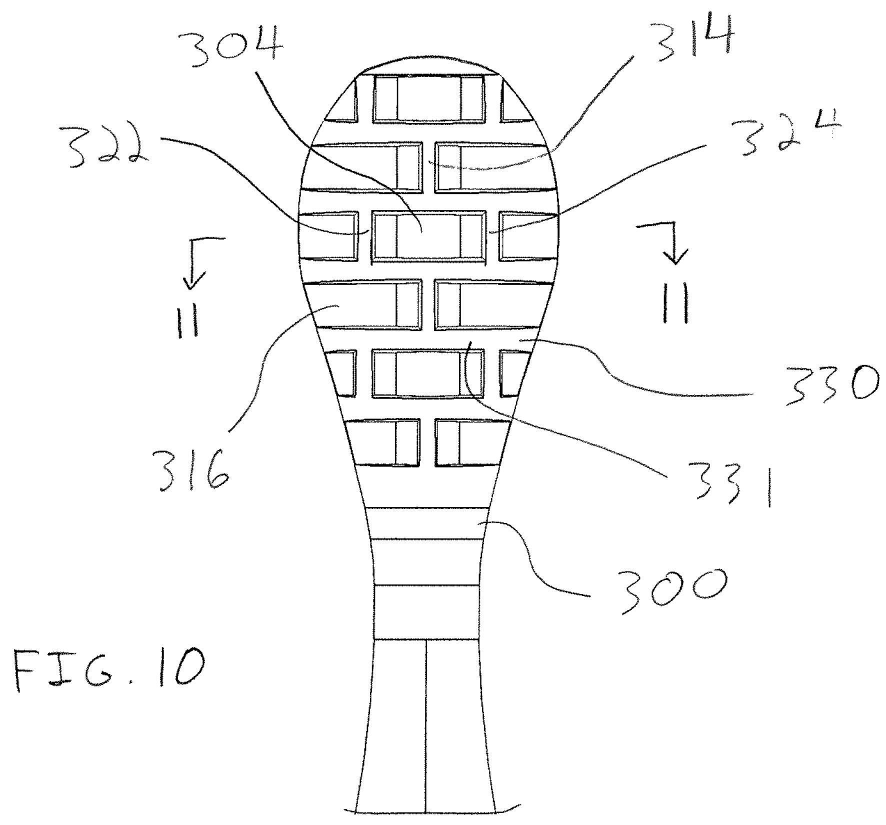
Figure 11:
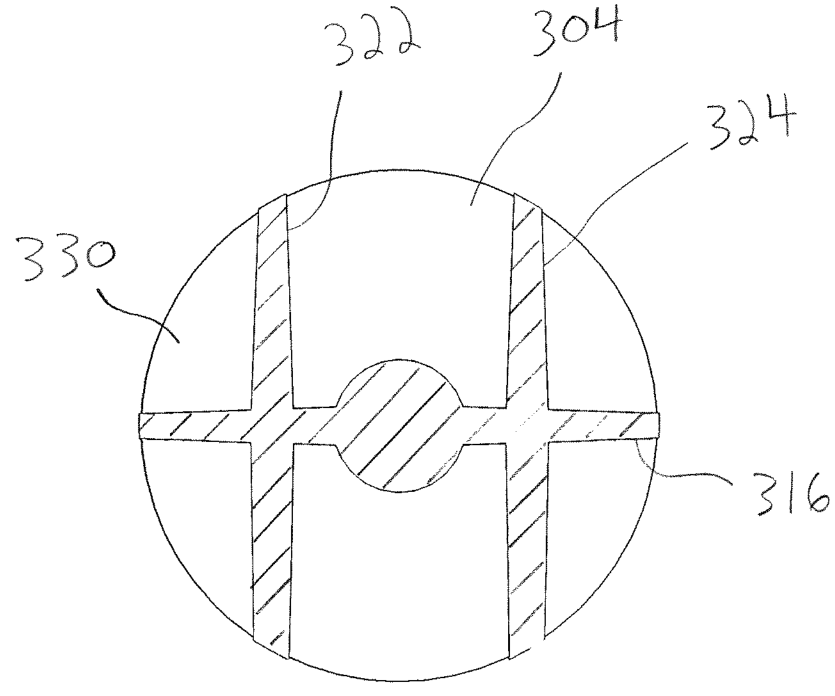
FIG. 11 is a cross-sectional view taken across line 11-11 in FIG. 10.

With reference to FIGS. 9-11, another head 300 for the ear cleaning device 10 is shown. The head 300 has a contiguous pocket structure 302 including a number of pockets 304 that are organized in a grid-like pattern with the pockets 304 offset along the length of the head in a manner similar to the pocket structure 202 of head 200. However, the pockets 304 are generally larger than the pockets 204 as seen by comparing FIGS. 6 and 9. More specifically, the pocket structure 302 includes rows 310 of pockets 304 along the length of the head 300 with some rows 312 having a single longitudinal wall 314 defining the pockets 304 in conjunction with the lateral walls 330 and some rows 320 having a pair of longitudinal walls 322, 324 defining the pockets 304 in conjunction with the lateral walls 330. Because of the longer uninterrupted lengths of edges 331 of the lateral walls 330 than the uninterrupted lengths of edges 211 of lateral walls 210 (see FIGS. 7 and 10), the edges 331 may provide enhanced debris removal with movement of the head 300 in longitudinal directions 332, as shown in FIG. 10.

Figure 12:
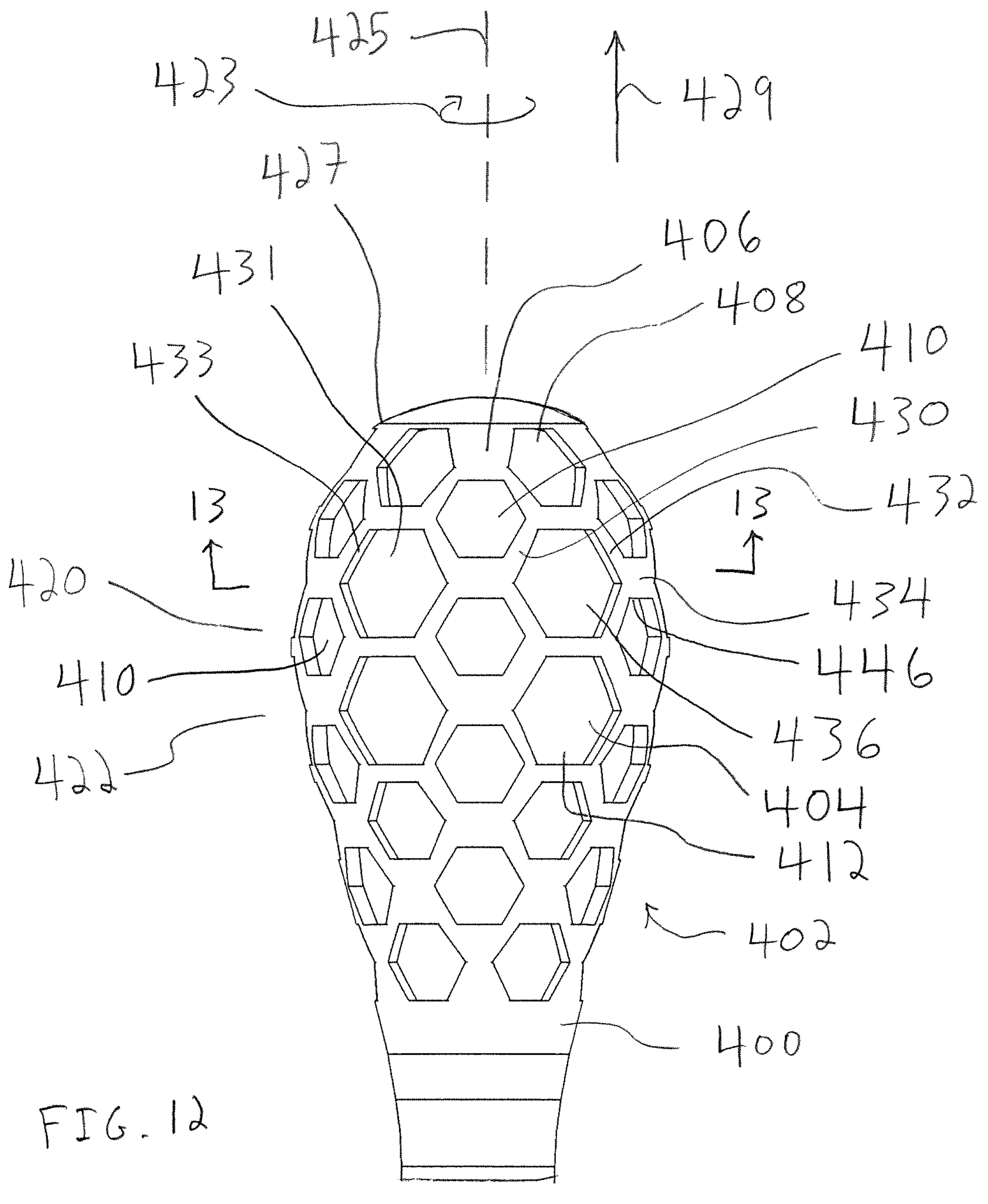
FIG. 12 is an elevational view of another head for the ear cleaning device of FIG. 1.
Figure 13:
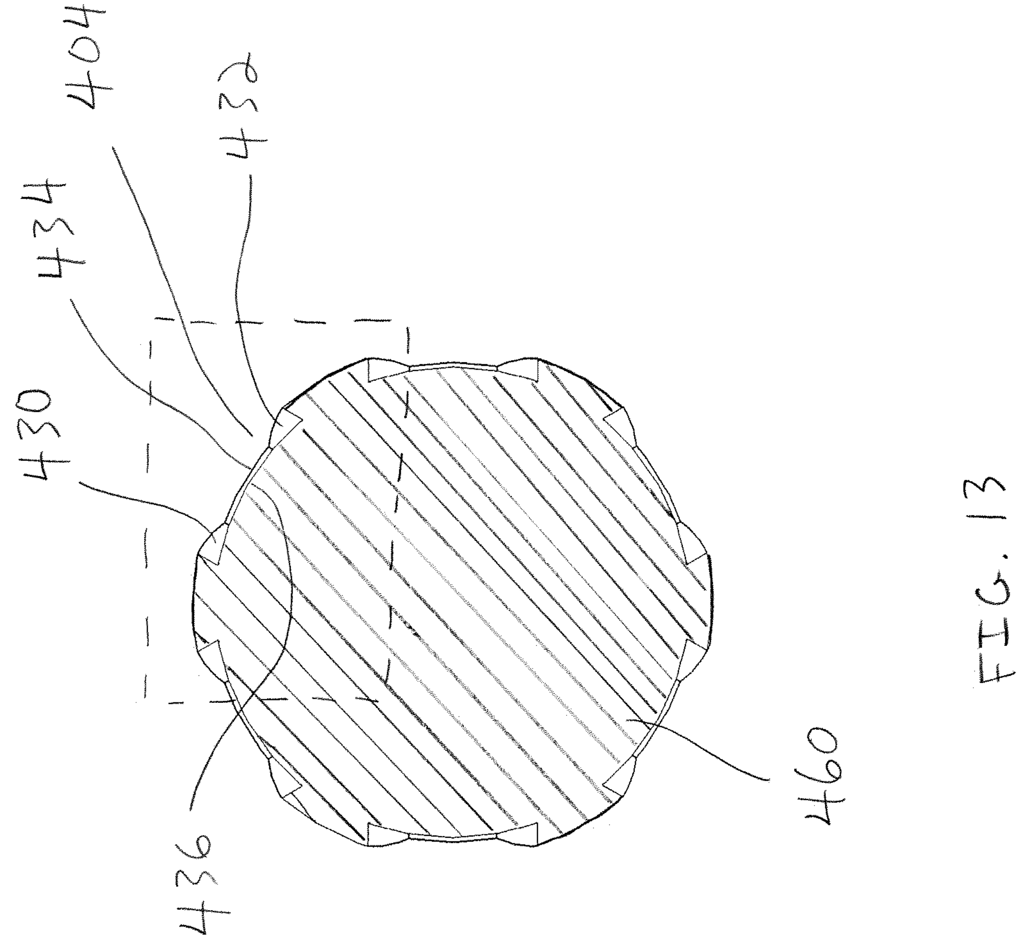
FIG. 13 is a cross-sectional view taken across line 13-13 in FIG. 12.
Figure 13A:
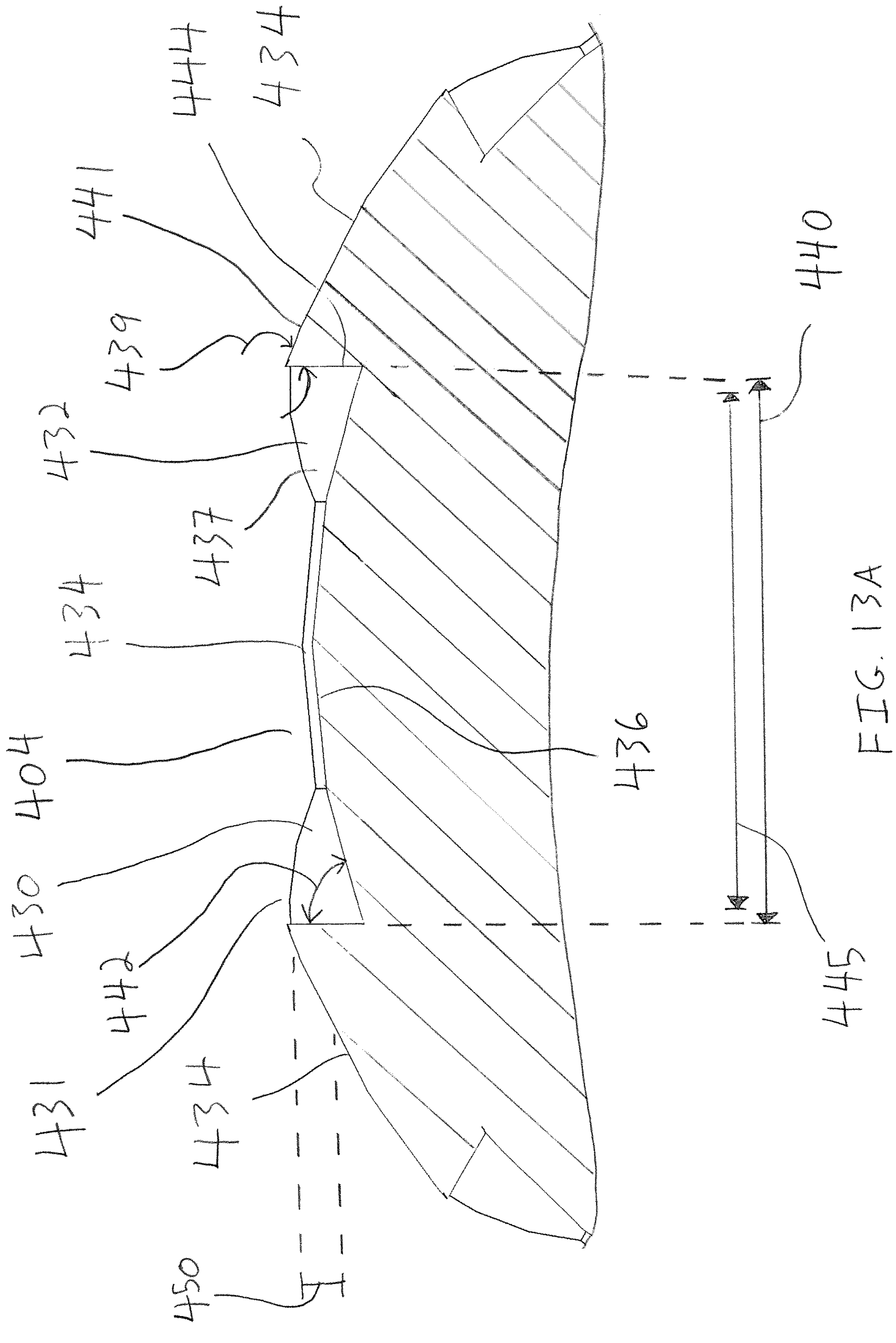
FIG. 13A is an enlarged view of the area shown in the dashed square of FIG. 13.

With reference to FIGS. 12-13A, another head 400 for the ear cleaning device 10 is shown. The head 400 is similar in many respects to the heads 20, 200, 300 discussed above such that differences between the head 400 and the head 20, 200, 300 will be discussed in detail. For example, the head 400 has a contiguous pocket structure 402 including a number of pockets 404 arranged in an alternating pattern about the head 400. More specifically, the pockets 404 include alternating columns 406, 408 of smaller pockets 410 and larger pockets 412, as shown in FIG. 12. The pocket structure 402 also includes alternating rows 420, 422 of smaller pockets 410 and larger pockets 412. The alternating pattern of the pockets 404 may provide a sequential presentation of the differently sized pockets 410, 412 against the surface of the ear with rotary or linear movement of the head 400 against the ear surface. This sequential presentation may cause the smaller pockets 410 to initially lift or remove the debris while the subsequently presented larger pockets 412 capture the debris for removal from the ear.

For example and with reference to FIG. 12, bringing the head 400 into contact with an ear surface and turning the head 400 in direction 423 about a longitudinal axis 425 of the head 400 brings one or more smaller pockets 410 of the column 406 into contact with the ear surface followed by one or more larger pockets 412 of the column 408. Similarly, a user may bring a distal end 427 of the head 400 into contact with a surface of the ear and then advance the head 400 in longitudinal direction 429 which brings one or more of the smaller pockets 410 of one of the rows 420 into contact with the ear surface followed by one or more of the larger pockets 412 of a more proximal row 422. This alternating presentation of the smaller and larger pockets 410, 412 may thereby be achieved with either linear or rotary movement of the head 400.

The pocket structure 402 includes longitudinal walls 430, 432 and lateral walls 434 that are upstanding from floors 436 of the pockets 404 and generally define the shape of openings 431 of the pockets 404, as shown in FIG. 12. The walls 430, 432, 434 have outer edges 433 extending about openings 431 of the pockets 404 for lifting or scraping debris into the pockets 404. Further, as shown in FIG. 13A, the pocket longitudinal and lateral walls 430, 432, and 434 are sized to provide a desired depth 450 of the pocket 404. However, the floor 436 may be convex with a varying depth such that the floor 436 tends to direct debris into corner recesses 444 of the pocket 404. The openings 431 have a shape similar to the shape of the respective floor 436, but are smaller than the floors 436, such that portions of the walls 430, 432, 434 extend inwardly over the floor 436 and form the corner recesses 444, as shown in FIG. 13A.

More specifically, the floors 436 have hexagonal shapes with widths 440 while the openings 431 have widths 445 that are smaller than the floor widths 440. The longitudinal walls 430, 432 are also oriented at acute angles 442 relative to the floor 436 such that the longitudinal walls 430, 432 extend inwardly over the floors 436 and form the corner recesses 444 which may serve to trap debris within the pockets 404, as shown in FIG. 13A. The lateral walls 434 may also be oriented to extend at a similar angle inward over the floor 406 to create corner recesses 446 (see FIG. 12) at the lateral walls 434 that are similar to the corner recesses 444. Due to the inwardly angled walls 430, 432, 434, the edges 433 of walls 430, 432, 434 include inner pocket surfaces 437 disposed at acute angles 439 relative to an outer surface 441 of the head 400, as shown in FIG. 13A. The edges 433 are relatively sharp, and function to lift debris from ear surfaces and operate in conjunction with the inclined inner pocket surfaces 437 which direct the debris toward the corner recesses 444 where the debris is retained for removal. Thus, the convex floor 436 and the inclined inner pocket surfaces 437 both tend to direct debris toward the corner recesses 444 as the debris enters the associated pocket 404.

Another difference between the head 400 and the heads discussed above is that the head 400 has a solid inner core 460 that fills substantially the entire cross section head 400, as shown in FIG. 13. The relatively large solid inner core 460 resists bending and twisting of the head 400. Further, the solid inner core 460 may be well suited for particular types of manufacturing, such as by laser cutting.

Figure 14:
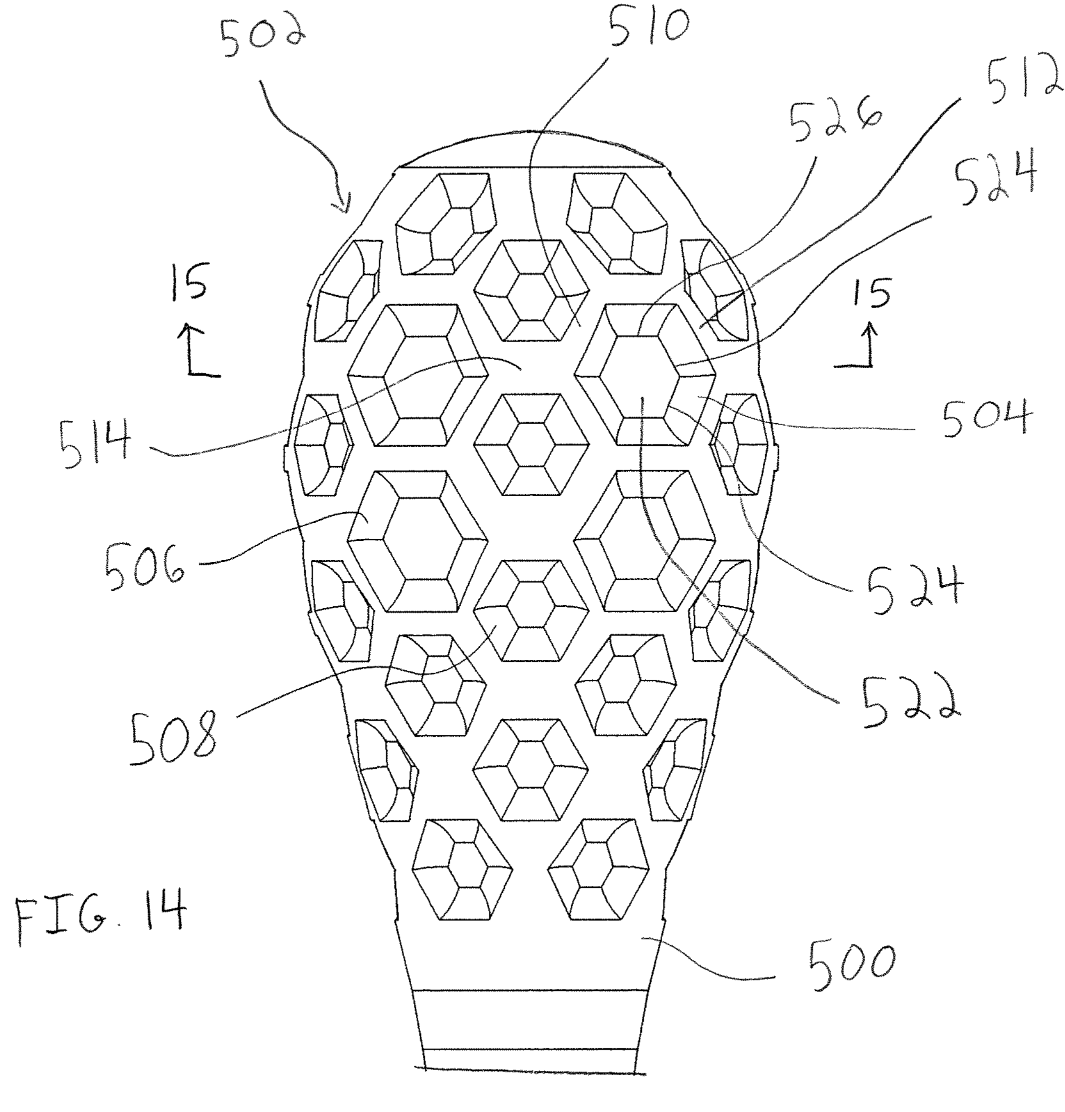
FIG. 14 is an elevational view of another head for the ear cleaning device of FIG. 1.
Figure 15:
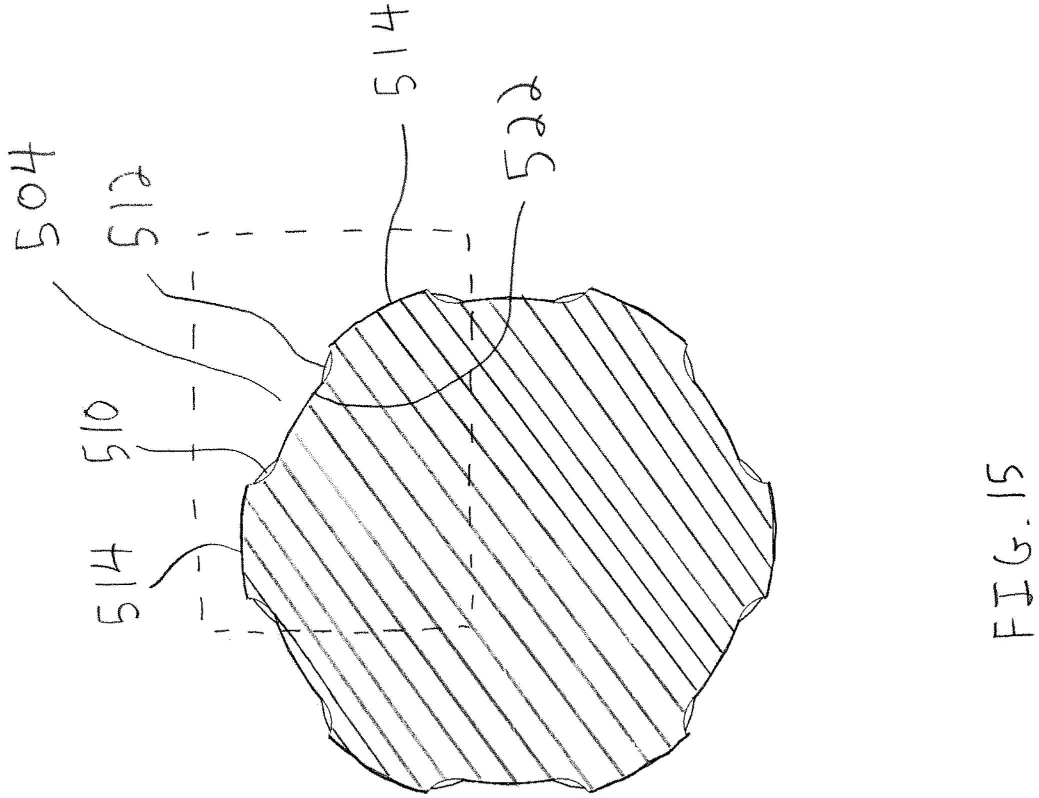
FIG. 15 is a cross-sectional view taken across line 15-15 in FIG. 14.
Figure 15A:
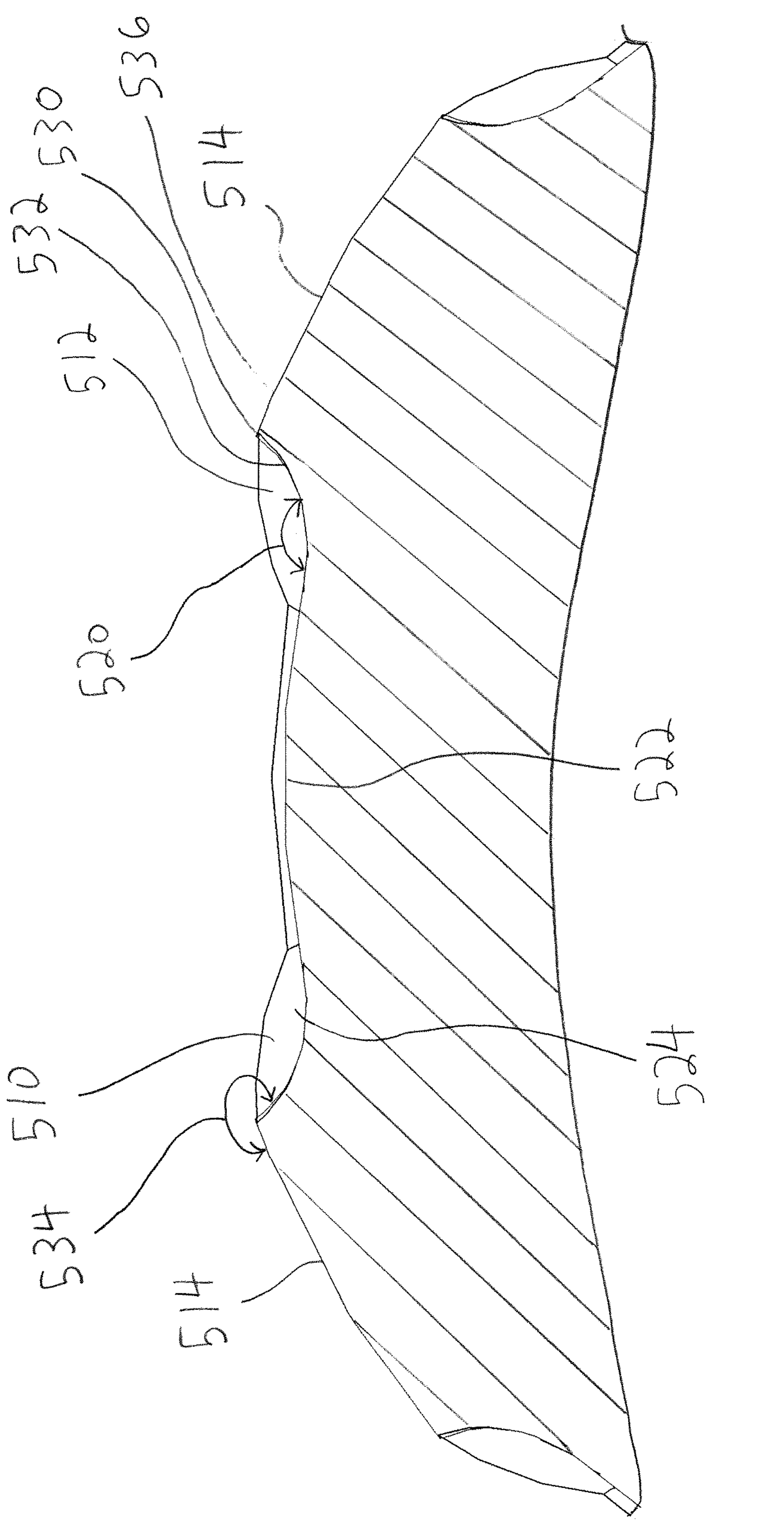
FIG. 15A is an enlarged view of the area shown in the dashed square of FIG. 15.

With reference to FIGS. 14-15A, another head 500 for the ear cleaning device 10 is shown. The head 500 is similar in many respects to the head 400 such that differences between the two will be highlighted. The head 500 includes a contiguous pocket structure 502 including a number of pockets 504 with larger pockets 506 and smaller pockets 508. The pocket structure 502 has longitudinal walls 510, 512 and lateral walls 514 that define the pockets 504. With reference to FIG. 15A, the head 500 is different from the head 400 in that the longitudinal walls 510, 512 are oriented to extend at an obtuse angle 520 relative to a floor 522 of the pocket 504. This orients the longitudinal walls 510, 512 such that they extend away from the floor 522 and form corner recesses 524 at junctures of the longitudinal walls 510, 512 and the floor 522 that are more open than the corner recesses 444. Further, the junctures of the walls 510, 512 and floor 522 may be curved to provide a smooth transition for debris as it travels inward along the walls 510, 512 and onto the floor 522, as shown in FIG. 15A.

With respect to FIG. 14, the lateral walls 514 extend at similar obtuse angles as the longitudinal walls 510, 512 relative to the floor 522 such that there are similar open corner recesses 526 at the lateral walls 514. Because the walls 510, 512, 514 extend away from, rather than over, the floors 522 of the pockets 504, the walls 510, 512, 514 have edges 530 including inner pocket surfaces 532 disposed at obtuse angles 534 relative to an outer head surface 536, as shown in FIG. 15A. The less aggressive edges 530 provide a gentler scraping action against the ear surfaces while still removing debris therefrom.

Figure 16:
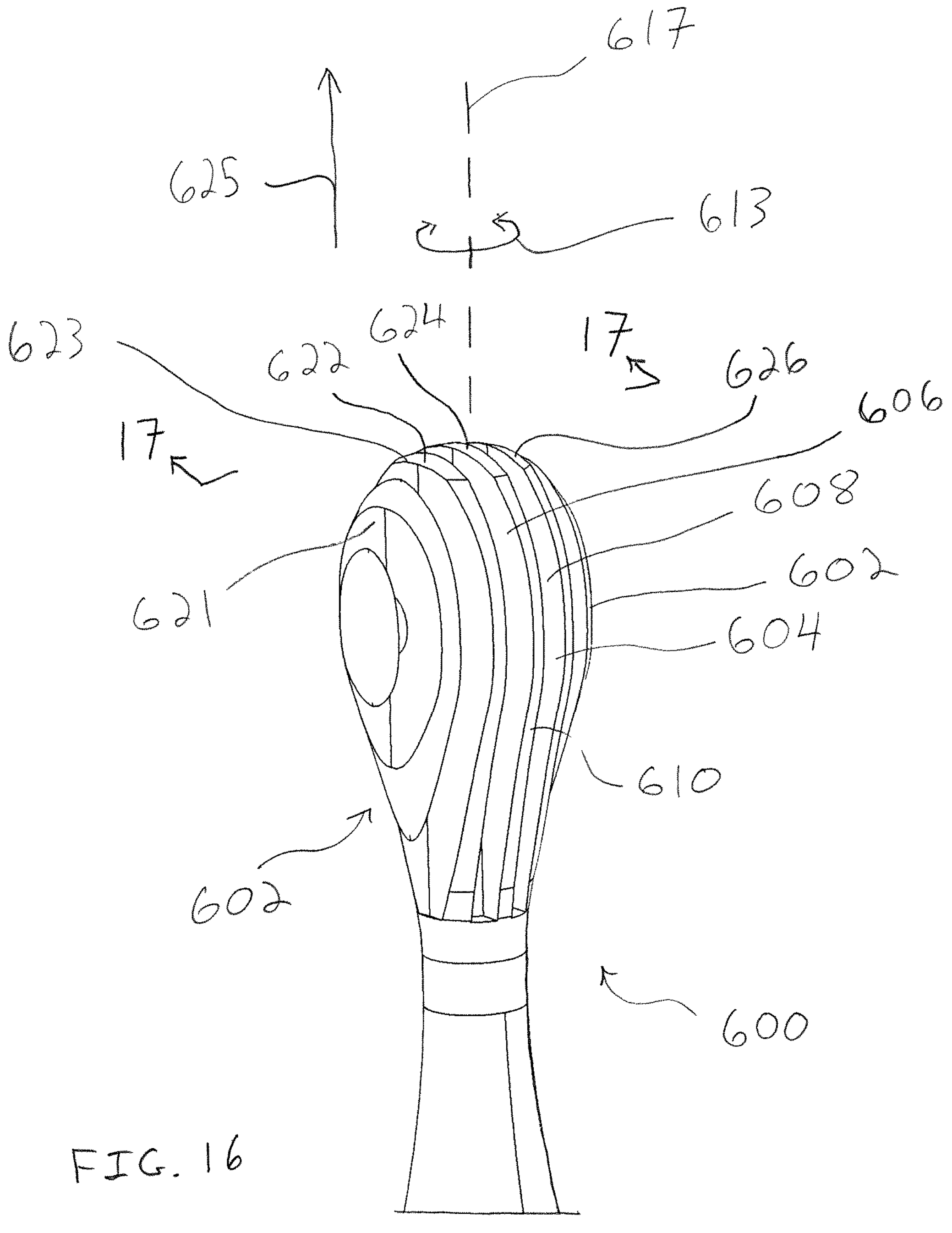
FIG. 16 is a perspective view of another head for the ear cleaning device of FIG. 1.

With reference to FIGS. 16-19, another head 600 for the ear cleaning device 10 is shown. The head 600 is similar to the head 20 in many respects and includes a contiguous pocket structure 602 having a number of pockets 604 configured to receive debris. The pocket structure 602 includes longitudinal walls 606 with longitudinal edges 610 configured to remove debris from an ear surface with turning of the head 600 in directions 613 about a longitudinal axis 617 of the head 600. As shown in FIG. 16, the longitudinal walls 606 further include leading ends 621 with transverse edges 623 for removing debris from an ear surface with generally linear movement of the head 600 in direction 625 along the longitudinal axis 617.

Figure 17:
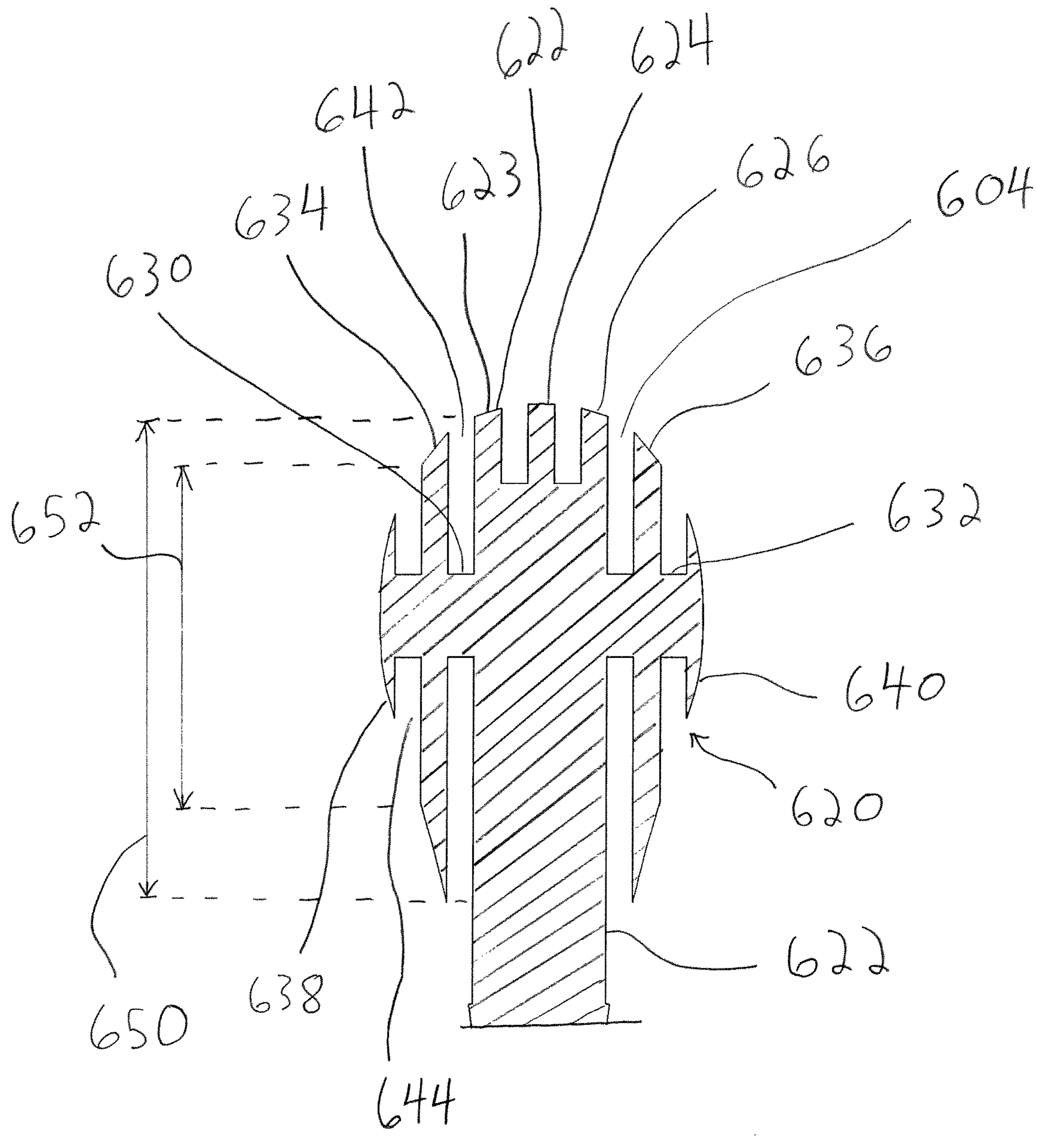
FIG. 17 is a cross-sectional view taken across line 17-17 in FIG. 16.
Figure 18:
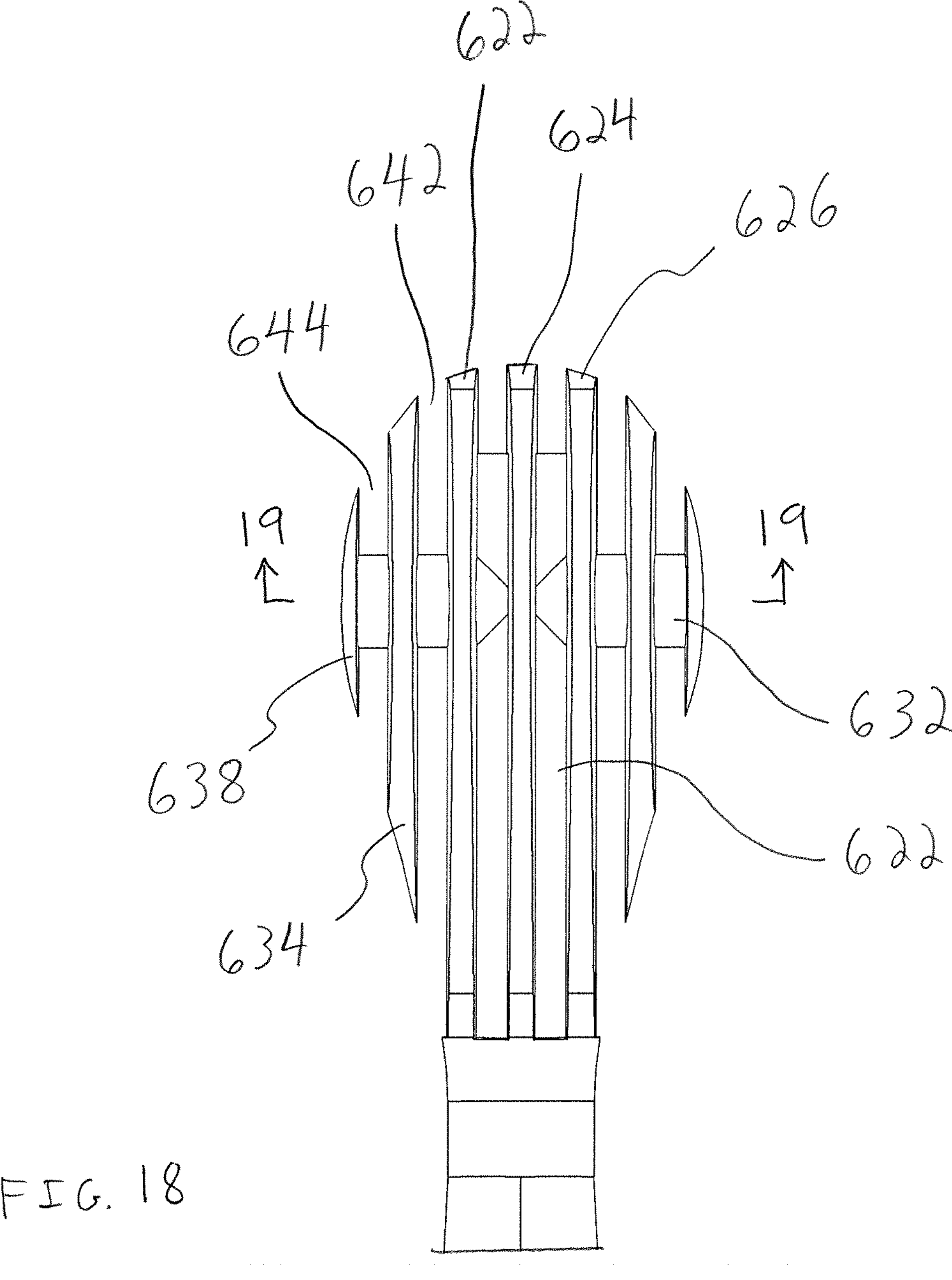
FIG. 18 is a front elevational view of the head of FIG. 16.

With reference to FIG. 17, the head 600 has a solid inner core 620 with a body 622 on which center longitudinal walls 622, 624, 626 are mounted and arms 630, 632 extending outward from the body 622 that form a generally t-shape of the solid inner core 620. The arms 630, 632 support side longitudinal walls 634, 636 and side caps 638, 640 of the head 600. The arms 630, 632 have a rounded configuration such that side pockets 642, 644 formed on either side of the longitudinal walls 634, 636 have a generally annular shape about the arms 630, 632. These annular side pockets 642, 644 have lengths 650, 652 sized to provide storage space for debris collected from the ear.

Figure 19:
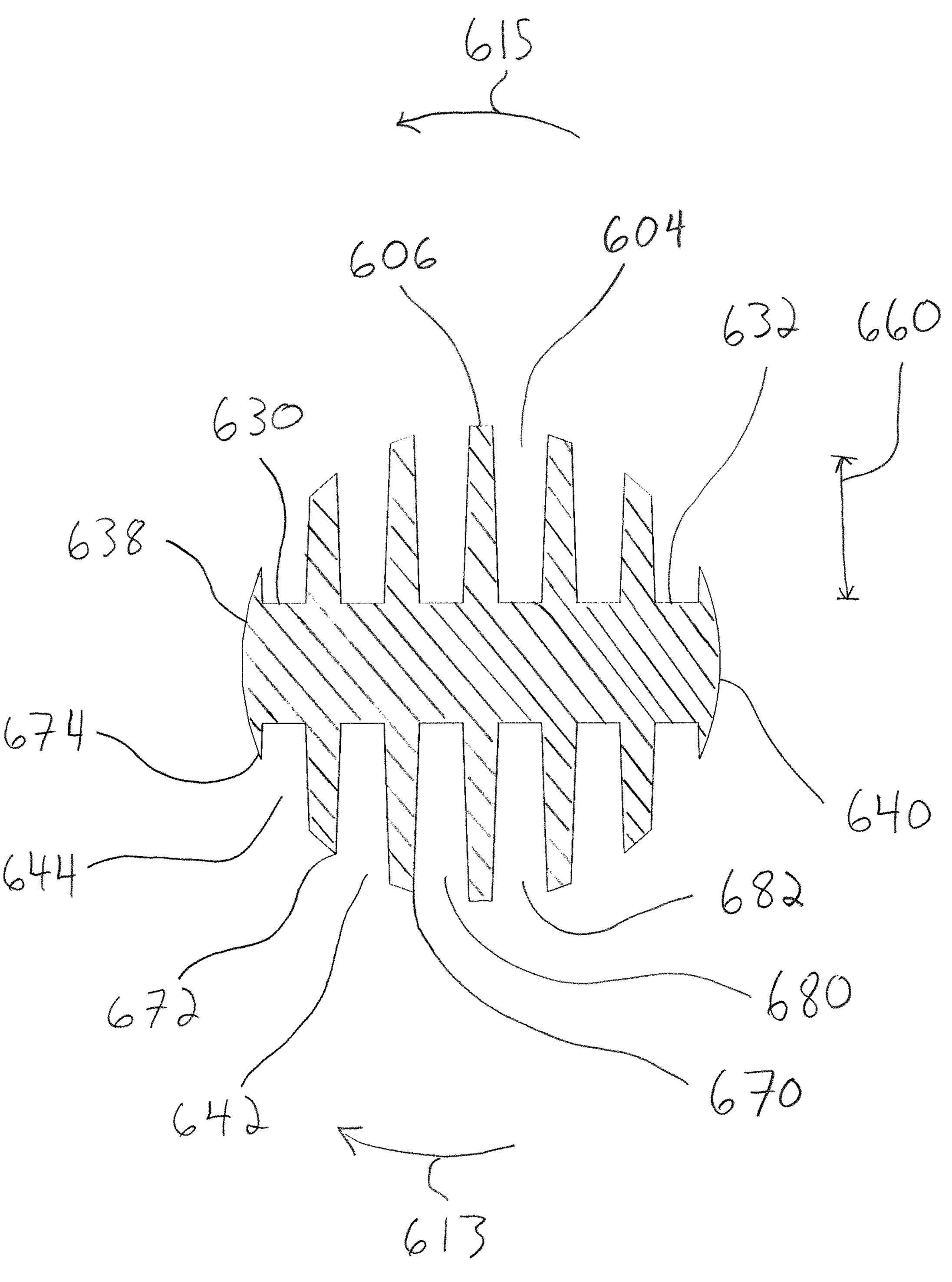
FIG. 19 is a cross-sectional view taken across line 19-19 in FIG. 18.
Figure 20:
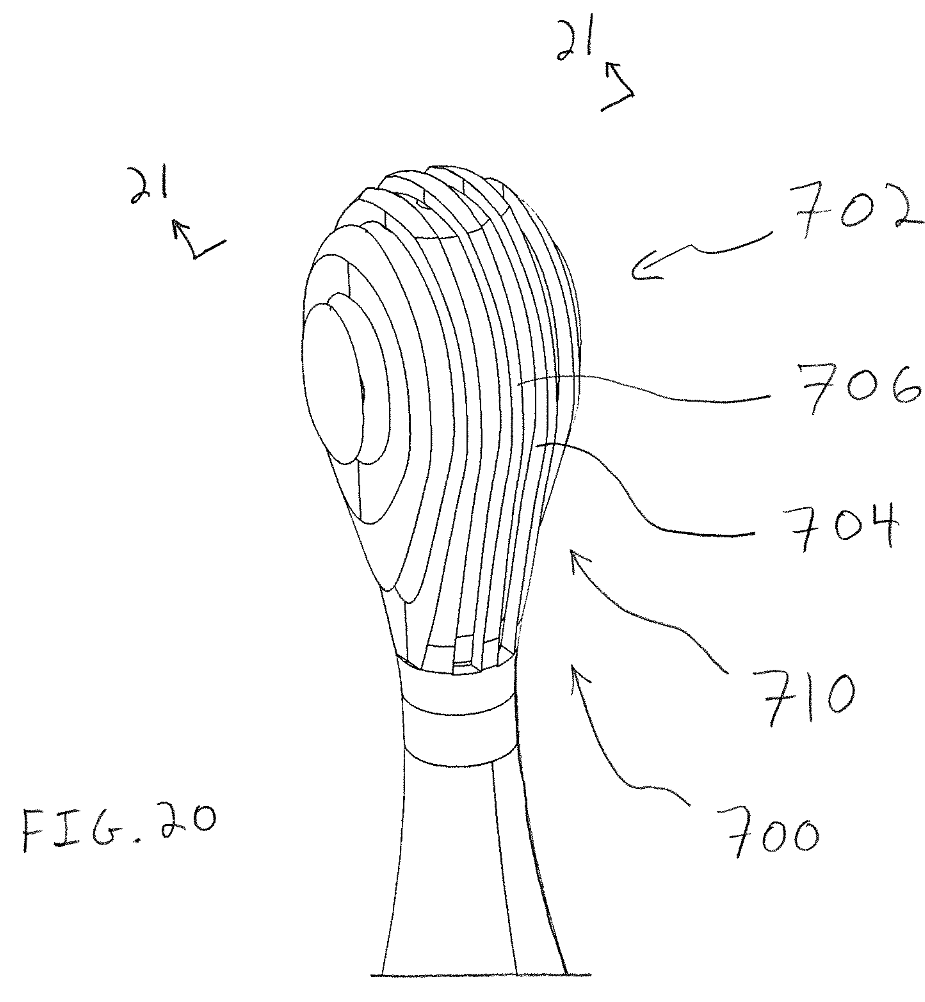
FIG. 20 is a perspective view of another head for the ear cleaning device of FIG. 1.
Figure 21:
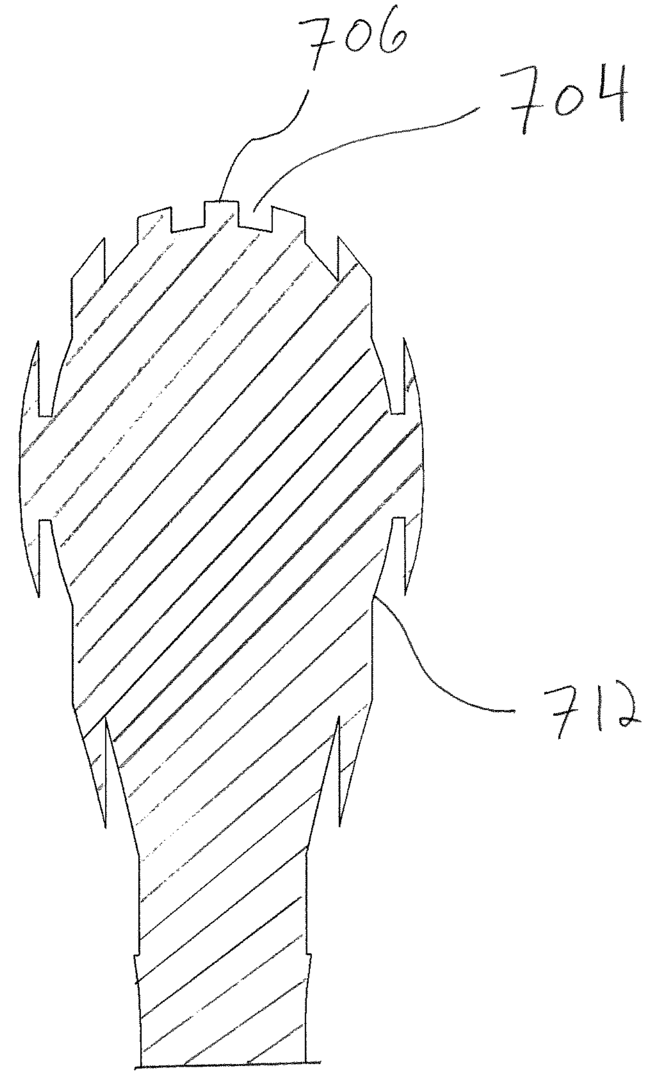
FIG. 21 is a cross-sectional view taken across line 21-21 in FIG. 20.
Figure 22:
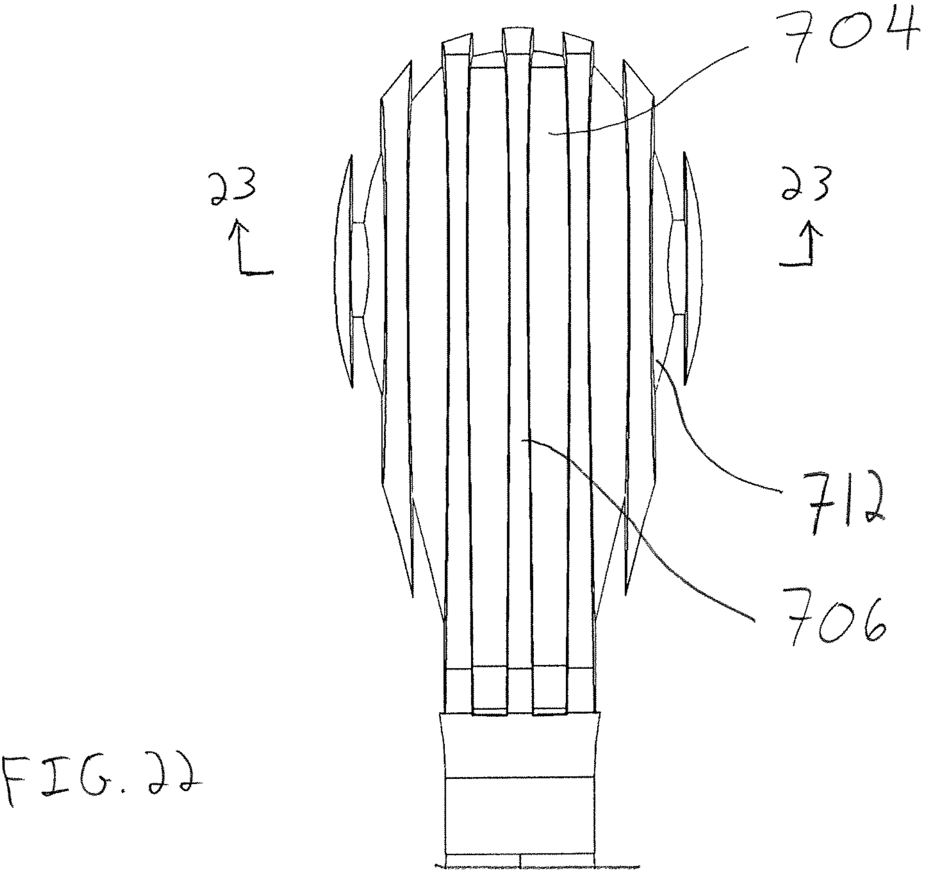
FIG. 22 is a front elevational view of the head of FIG. 20.
Figure 23:
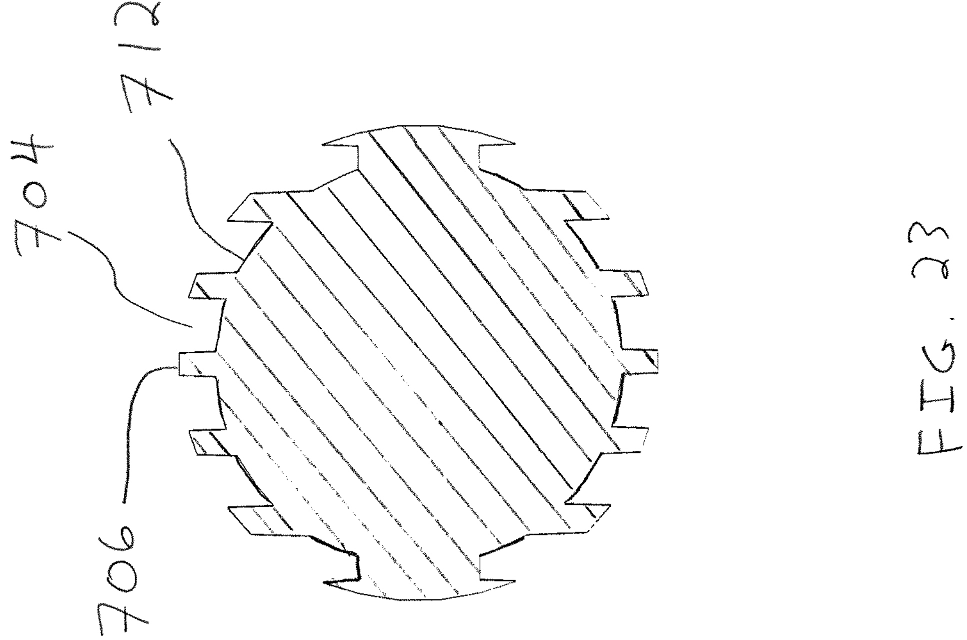
FIG. 23 is a cross-sectional view taken across line 23-23 in FIG. 22.

With reference to FIG. 19, the longitudinal walls 606 extend away from the arms 630, 632 on either side thereof. The pockets 604 generally have depths 660 that decrease heading away from the center of the head 600 while edges 670, 672, 674 become increasingly sharp heading away from the center of the head 600, as shown in FIG. 19. The sharper edges 672, 674 associated with the side pockets 642, 644 provide greater scraping action while deeper, center pockets 680, 682 (see FIG. 19) provide greater debris retention.

With reference to FIGS. 20-23, another head 700 for the ear cleaning device 10 is shown. The head 700 is similar in many respects to the head 600 and includes a contiguous pocket structure 702 including a number of pockets 704 and longitudinal walls 706 that define portions of the pockets 704. The head 700 is different from the head 600 in that the head 700 has a solid inner core 710 with a generally a bulbous body 712 rather than the body 622 and arms 630, 632 of head 600. The bulbous body 712 takes up more volume within the head 700 than the body 622 takes up within the head 600 such that the pockets 704 are shallower than the pockets 604. This configuration may be used in some applications where a more rigid head 700 for resisting bending and twisting is desired.

Figure 24:
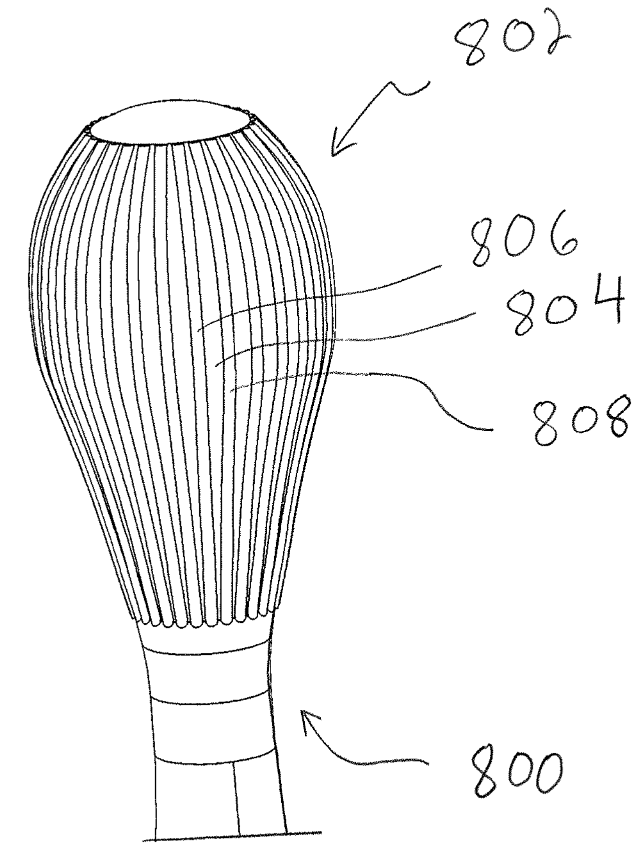
FIG. 24 is a perspective view of another head for the ear cleaning device of FIG. 1.
Figure 25:
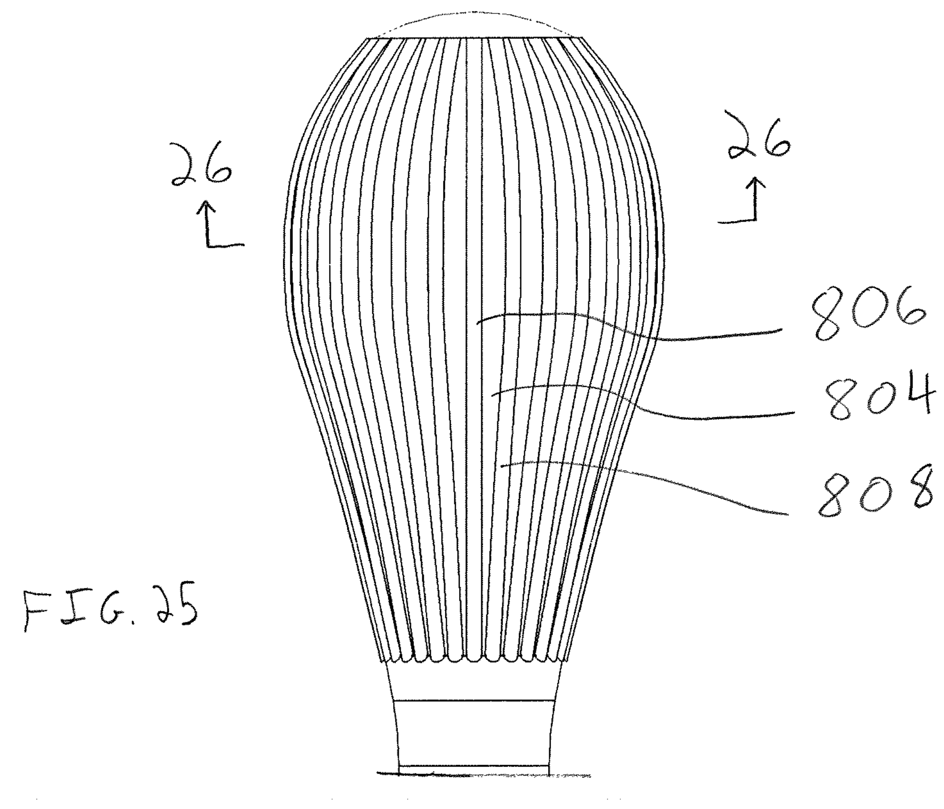
FIG. 25 is an elevational view of the head of FIG. 24.
Figure 26:
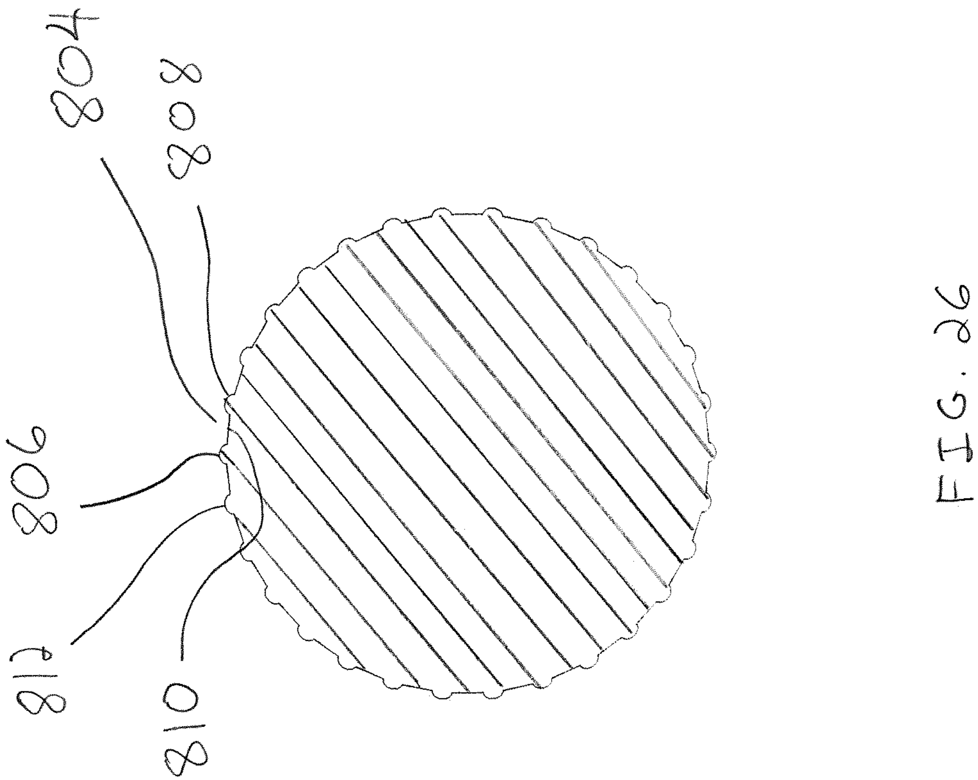
FIG. 26 is a cross-sectional view taken across line 26-26 in FIG. 25.

With respect to FIGS. 24-26, another head 800 for the ear cleaning device 10 is shown. The head 800 has a pocket structure 802 with a number of pockets 804 and longitudinal walls 806, 808 that define portions of the pockets 804. With reference to FIG. 26, the pockets 804 are different than the previously described pockets in that the walls 806, 808 are upstanding from floors 810 that extend substantially the entire length of the head 800. Further, the pockets 804 are different because the longitudinal walls 806, 808 have semi-circular outer edges 812 for lifting or scraping debris from ear surfaces.

Figure 27:
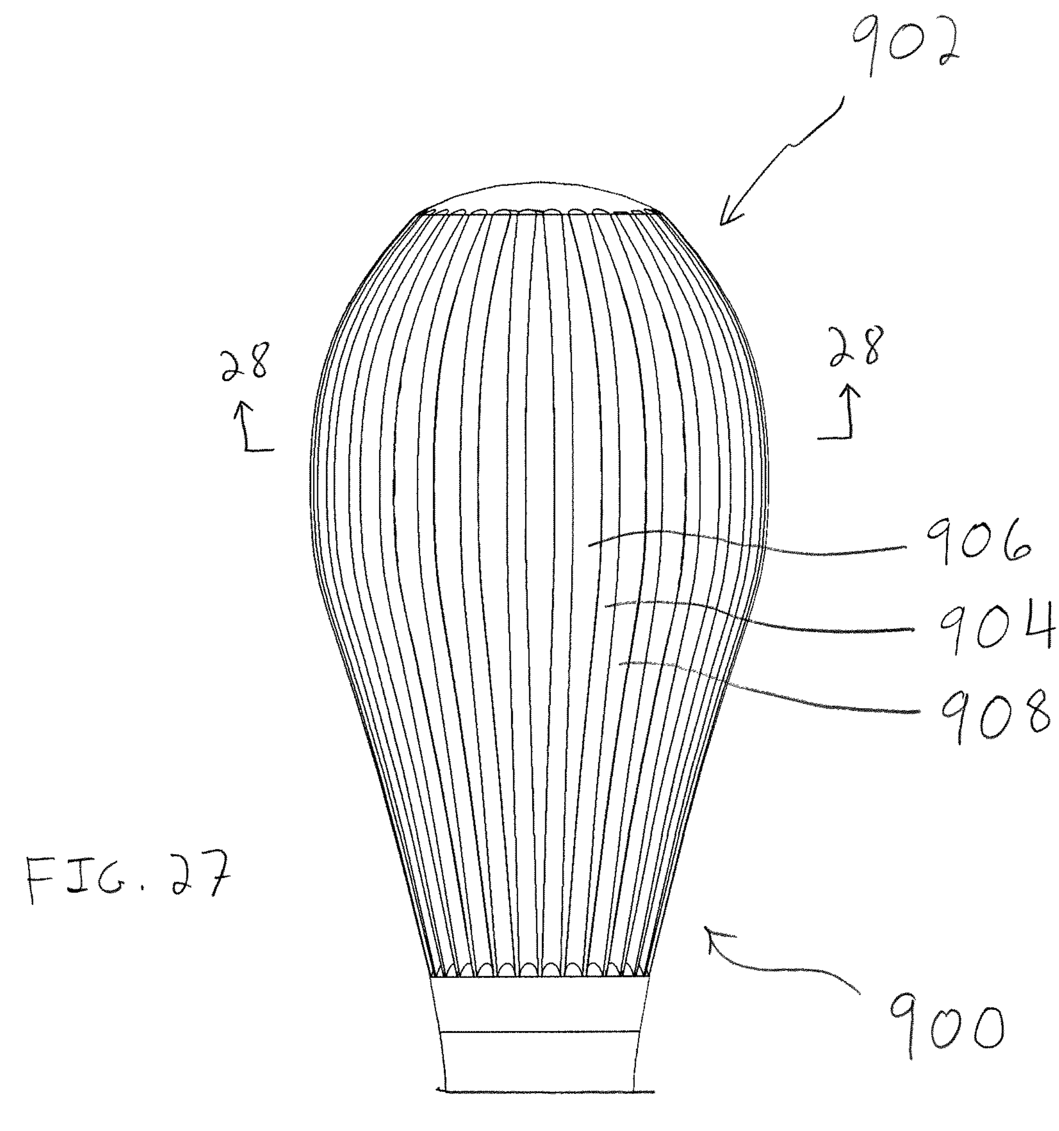
FIG. 27 is an elevational view of another head for the ear cleaning device of FIG. 1.
Figure 28:
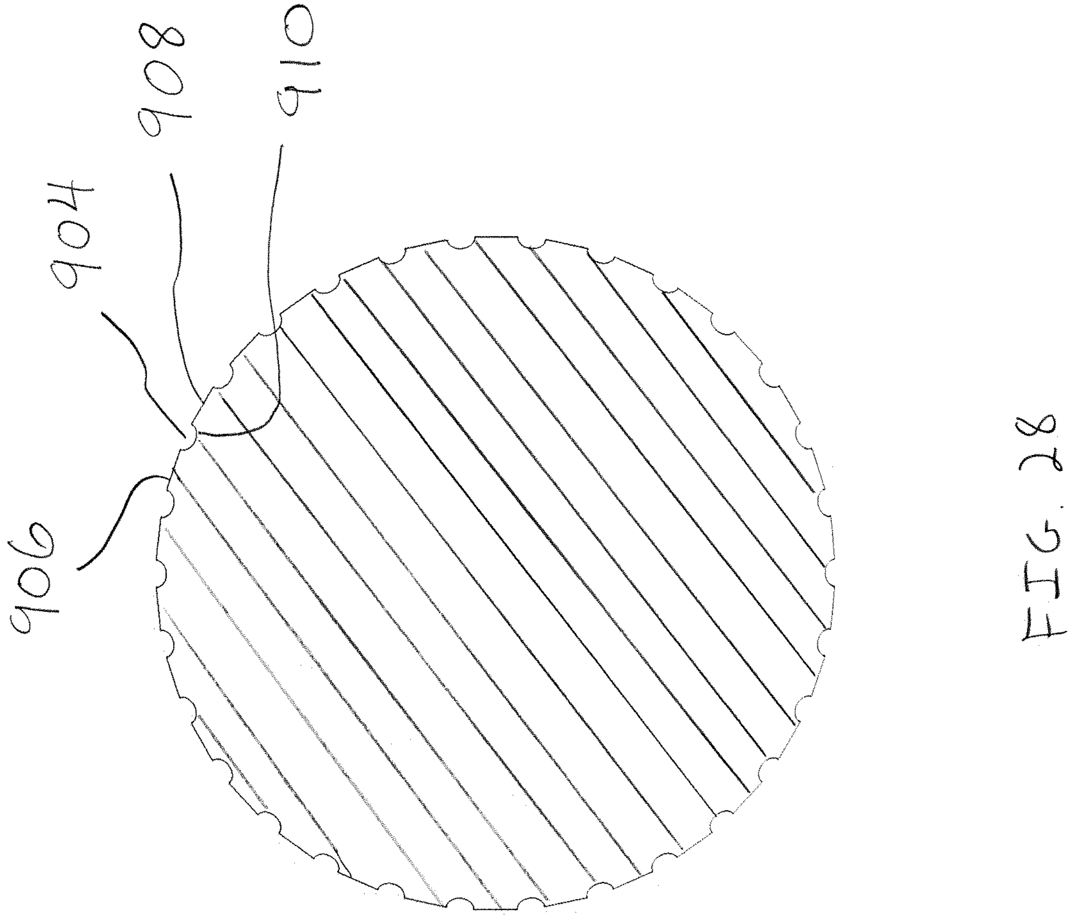
FIG. 28 is a cross-sectional view taken across line 28-28 in FIG. 27.

Turning to FIGS. 27 and 28, another head 900 for the ear cleaning device 10 is shown. The head 900 is substantially similar to head 800 such that differences between the two will be highlighted. The head 900 has a contiguous pocket structure 902 with a number of pockets 904 and longitudinal walls 906, 908 that define portions of the pockets 904. However, the pockets 904 include concave grooves 910 intermediate the walls 906, 908 rather than the convex floors 812.

Figure 29:
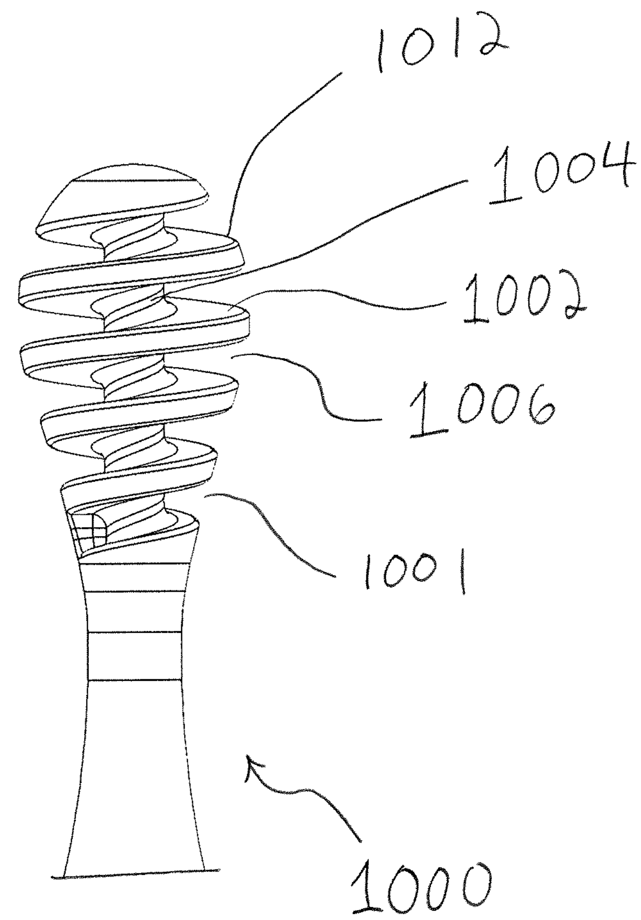
FIG. 29 is an elevational view of another head for the ear cleaning device of FIG. 1.
Figure 30:
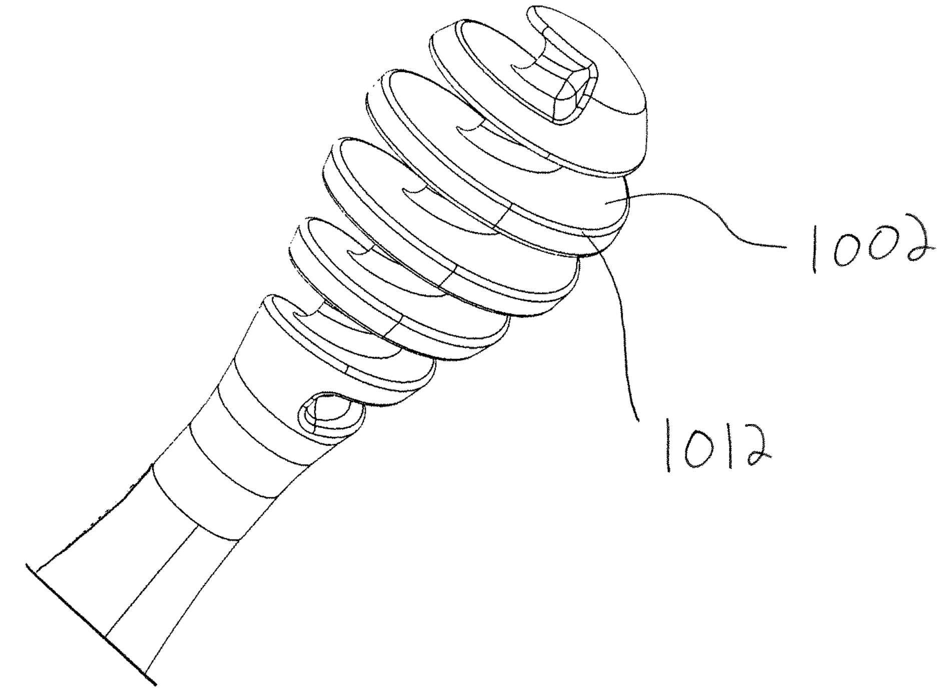
FIG. 30 is a perspective view of the head of FIG. 29.

Another head 1000 for the ear cleaning device 10 is illustrated in FIGS. 29 and 30. The head 1000 has screw-like configuration including a contiguous pocket structure 1001, threads 1002, and a solid inner core 1004. The threads 1002 define a pocket 1006 for receiving debris from ear surfaces. The threads 1002 have outer edges 1012 that can remove debris via linear movement of the head 1000. Alternatively, the user can turn the head 1000 in a rotary manner which causes the threads 1002 to act as a screw-type conveyor and withdraw the debris from the ear.

The ear cleaning device 10 can be made from a variety of materials such as plastic, steel, wood, and paper pulp-fibrous. The device 10 can be made of one or more materials. In one form, the ear cleaning device 10 is made of plastic and formed using an injection molding procedure.

While the foregoing description is with respect to specific examples, those skilled in the art will appreciate that there are numerous variations of the above that fall within the scope of the concepts described herein and the appended claims.

What is claimed is:

1. An ear cleaning device having a central, longitudinal axis, the ear cleaning device comprising:

an elongate body having a unitary, one-piece construction, the body including a pair of ear cleaners at opposite ends of the body, the body including a handle intermediate the ear cleaners;

at least one ear cleaner of the pair of ear cleaners including an elongate head configured to fit in a human ear, the head having a length extending along the longitudinal axis;

the head having a bulbous exterior shape;

the head including an inner shaft and a helical thread extending about the inner shaft;

the head having a trailing end connected to the handle and a leading end opposite the trailing end;

the helical thread of the head comprising:

a leading turn of the helical thread adjacent the leading end of the head, the leading turn having a first width perpendicular to the longitudinal axis;

a trailing turn of the helical thread adjacent the trailing end of the head, the trailing turn having a second width perpendicular to the longitudinal axis; and an intermediate turn of the helical thread intermediate the leading turn and the trailing turn along the length of the head, the intermediate turn having a third width perpendicular to the longitudinal axis that is larger than the first width and is larger than the second width.

2. The ear cleaning device of claim 1 wherein the helical thread comprises a pair of helical scraping edges extending from the leading end to the trailing end of the head.

3. The ear cleaning device of claim 2 wherein the helical thread comprises:

an inboard helical surface extending from the inner shaft to one of the helical edges; and an outboard helical surface extending from the inner shaft to the other of the helical edges, the outboard helical surface on an opposite side of the helical thread than the inboard helical surface.

4. The ear cleaning device of claim 3 wherein the helical thread comprises a radially outer, helical surface connecting the helical scraping edges.

5. The ear cleaning device of claim 1 wherein the helical thread comprises a pair of helical scraping edges extending from the leading end to the trailing end of the head; and wherein the helical thread includes a helical outer surface connecting the edges and defining at least a portion of the bulbous exterior shape of the head.

6. The ear cleaning device of claim 1 wherein the head includes a helical groove extending around the inner shaft from the leading end to the trailing end, the helical groove defined at least in part by the helical thread and the inner shaft.

7. The ear cleaning device of claim 6 wherein the helical groove has a closed end at the leading end of the head.

8. The ear cleaning device of claim 6 wherein the helical groove has a closed end at the trailing end of the head.

9. The ear cleaning device of claim 1 wherein the leading end of the head includes a terminal outward convex surface.

10. The ear cleaning device of claim 1 wherein the leading end of the head includes a wall extending radially from the inner shaft; and wherein the helical thread includes a leading end portion that extends away from the wall and around the inner shaft.

11. The ear cleaning device of claim 1 wherein the helical thread comprises a pair of helical scraping edges extending from the leading end to the trailing end of the head; and wherein the head includes an axial scraping edge extending from the leading end of the head to one of the helical scraping edges.

12. The ear cleaning device of claim 1 wherein the intermediate turn of the helical thread extends completely around the inner shaft.

13. The ear cleaning device of claim 1 wherein the helical thread is a single helical thread that extends from the leading end to the trailing end of the head.

14. The ear cleaning device of claim 1 wherein the ear cleaning device is made of an inedible material.

* * * * *